US006217863B1

(12) United States Patent
Godavarti et al.

(10) Patent No.: US 6,217,863 B1
(45) Date of Patent: Apr. 17, 2001

(54) RATIONALLY DESIGNED POLYSACCHARIDE LYASES DERIVED FROM HEPARINASE I

(75) Inventors: Ranganathan Godavarti, Somerville; Ram Sasisekharan, Cambridge, both of MA (US); Steffen Ernst, Hellerup (DK); Ganesh Venkataraman, Somerville, MA (US); Charles L. Cooney, Brookline, MA (US); Robert Langer, Newton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/066,481

(22) PCT Filed: Oct. 30, 1996

(86) PCT No.: PCT/US96/17310

§ 371 Date: Jan. 19, 1999

§ 102(e) Date: Jan. 19, 1999

(87) PCT Pub. No.: WO97/16556

PCT Pub. Date: May 9, 1997

Related U.S. Application Data

(60) Provisional application No. 60/008,069, filed on Oct. 30, 1995.

(51) Int. Cl.[7] .............................. A61K 38/51; C12N 9/88; C07H 21/04
(52) U.S. Cl. .......................... 424/94.5; 435/2; 435/232; 435/252.33; 435/320.1; 536/23.2
(58) Field of Search .............................. 435/232, 252.3, 435/252.33, 320.1, 2, 267; 536/23.1, 23.2; 424/94.5

(56) References Cited

U.S. PATENT DOCUMENTS

| | | | |
|---|---|---|---|
| 4,281,108 | 7/1981 | Fussi | 536/21 |
| 4,341,869 | 7/1982 | Langer, Jr. et al. | 435/232 |
| 4,373,023 | 2/1983 | Langer et al. | 435/2 |
| 4,396,762 | 8/1983 | Langer et al. | 536/21 |
| 4,443,545 | 4/1984 | Langer, Jr. et al. | 435/232 |
| 4,745,105 | 5/1988 | Griffin et al. | 514/56 |
| 4,757,056 | 7/1988 | Van Gorp et al. | 514/54 |
| 4,942,156 | 7/1990 | Foley et al. | 514/56 |
| 4,990,502 | 2/1991 | Lormeau et al. | 514/56 |
| 5,010,063 | 4/1991 | Piani et al. | 514/56 |
| 5,039,529 | 8/1991 | Bergendal et al. | 424/630 |
| 5,106,734 | 4/1992 | Nielsen | 435/84 |
| 5,152,784 | 10/1992 | Tsilibary | 623/1 |
| 5,164,378 | 11/1992 | Conti et al. | 514/56 |
| 5,169,772 | 12/1992 | Zimmerman et al. | 435/232 |
| 5,204,323 | 4/1993 | Findlay et al. | 514/2 |
| 5,252,339 | 10/1993 | Cristofori et al. | 424/479 |
| 5,262,325 | 11/1993 | Zimmermann et al. | 435/269 |
| 5,290,695 | 3/1994 | Morikawa et al. | 435/232 |
| 5,338,677 | 8/1994 | Zimmermann et al. | 435/200 |
| 5,389,539 | 2/1995 | Sasisekharan et al. | 435/220 |
| 5,474,987 | 12/1995 | Cohen et al. | 514/56 |
| 5,567,417 | 10/1996 | Sasisekharan et al. | 424/94.5 |
| 5,569,600 | 10/1996 | Sasisekharan et al. | 435/220 |
| 5,576,304 | 11/1996 | Kakkar et al. | 514/56 |
| 5,599,801 | 2/1997 | Branellec et al. | 514/56 |
| 5,618,917 | 4/1997 | Toback et al. | 530/350 |
| 5,619,421 | 4/1997 | Venkataraman et al. | 346/496 |
| 5,681,733 | 10/1997 | Su et al. | 435/232 |
| 5,714,376 | 2/1998 | Sasisekharan et al. | 435/252.3 |
| 5,744,515 | 4/1998 | Clapper | 523/113 |
| 5,753,445 | 5/1998 | Fillit et al. | 435/7.1 |
| 5,763,427 | 6/1998 | Weitz et al. | 514/56 |
| 5,795,875 | 8/1998 | Holme et al. | 514/56 |
| 5,808,021 | 9/1998 | Holme et al. | 536/21 |
| 5,824,299 | 10/1998 | Luster et al. | 424/85.1 |
| 5,830,726 | 11/1998 | Sasisekharan et al. | 435/172.3 |
| 5,919,693 | 7/1999 | Su et al. | 435/252.3 |
| 5,922,358 | 7/1999 | Doutremepuich et al. | 424/553 |
| 5,997,863 | 12/1999 | Zimmerman et al. | 424/94.5 |
| 6,013,628 | 1/2000 | Skubitz et al. | 513/12 |

FOREIGN PATENT DOCUMENTS

| | | |
|---|---|---|
| 0 433 225 A1 | 11/1990 | (EP) . |
| 0 557 887 A2 | 2/1993 | (EP) . |
| WO93/08289 | 4/1993 | (WO) . |
| WO 93/19096 | 9/1993 | (WO) . |
| WO 94/21689 | 9/1994 | (WO) . |
| PCT/US96/17310 | 10/1996 | (WO) . |
| WO 97/16556 | 5/1997 | (WO) . |

OTHER PUBLICATIONS

Karen A. Valentine, M.D. et al., "Low–Molecular–Weight Heparin Therapy and Mortality," *Seminars in Thrombosis and Hemostasis,* vol. 23, No. 2, 1997, pp. 173–178.

Robert J. Linhardt, Ph.D. et al., "Production and Chemical Processing of Low Molecular Weight Heparins," *Seminars in Thrombosis and Hemostasis,* vol. 25, Suppl. 3, 1999, pp. 5–16.

James N. Huang, MD. et al., "Low–Molecular–Weight Heparins", *Coagulation Disorders,* vol. 12, No. 6, Dec. 1998, pp. 1251–1277.

Richard L. Jackson et al., "Glycosaminoglycans: Molecular Properties, Protein Interactions, and Role in Physiological Processes", *Reviews,* vol. 71, No. 2, Apr., 1991, pp. 481–539.

Gerald W. Hart, "Glycosylation", *Current Opinion in Cell Biology,* 1992, 4:1017–1023.

Pita Enriquez–Harris et al., "Growth Factors and the Extracellular Matrix", *Meeting Report,* Trends in Cell Biology, 1994.

(List continued on next page.)

*Primary Examiner*—Nashaat T. Nashed
(74) *Attorney, Agent, or Firm*—Wolf, Greenfield & Sacks, P.C.

(57) ABSTRACT

Modified heparinases having altered binding specificity and activity are provided. Isolated nucleic acids encoding the same as as vectors and host cells are provided. Methods for using the modified heparinases are also provided.

18 Claims, 2 Drawing Sheets

OTHER PUBLICATIONS

Fred E. Cohen, The Parallel β Helix of Pectate Lyase C: Something to Sneeze At, *Science,* vol. 260, Jun. 4, 1993, pp. 1444–1445.

Ulrich Baumann et al., "Three–dimensional structure of the alkaline protease of *Pseudomonas aeruginosa:* a calcium binding parallel beta roll motif", *The EMBO Journal,* vol 12, No. 9, pp. 3357–3364, 1993.

Marilyn D. Yoder et al., "Unusual structural features in the parallel β–helix in pectate lyases", *Structure,* Dec. 15, 1993, 1:241–251.

Marilyn D. Yoder et al., "New Domain Motif: The Structure of Pectate Lyase C., a Secreted Plant Virluence Factor", *Science,* vol 260, Jun. 4, 1993, pp. 1503–1506.

Michael J. Franklin et al, "*Pseudomonas aeruginosa* AlgG is a Polymer Level Alginate C5–Mannuronan Epimerase", *Journal of Bacteriology,* vol. 176, No. 7, Apr. 1994, p. 1821–1830.

David Sidney Feingold et al., "Conformational aspects of the reaction mechanisms of polysaccharide lyases and epimerases," *FEBS Letters,* vol. 223, No. 2, Nov., 1987, pp. 207–211.

Peter Gacesa, "Alginate–modifying enzymes—A proposed unified mechanism of action for the lyases and and epimerases", *FEBS LETTERS,* vol. 212, No. 2, Feb., 1987, pp. 199–202.

Florentyna Lustig et al., "Alternative Splicing Determines the Binding of Platelet–Derived Growth Factor (PDGF–AA) to Glycosaminoglycans", *Biochemistry,* vol. 35, No. 37 1996, pp. 12077–12085.

Ranga Godavarti et al., "Heparinase I from *Flavobacterium heparinum.* Identification of a Critical Histidine Residue Essential for Catalysis As Probed by Chemical Modification and Site–Directed Mutagensis" *Biochemistry,* 1996, 35, 6846–6852.

Ram Sasisekharan et al., "Heparinase I from *Falbobacterium heparinum"*, *The Journal of Biological Chemistry,* vol. 271 No. 6, Issue Feb. 9, pp. 3124–3131.

Ram Sasisekharan et al., "Heparinase I from *Flavobacterium heparinum"* The Role of the Cysteine–Residue in Catalysis as Probed by Chemical Modifications and Site–Directed Mutagenesis, *Biochemistry,* vol. 34, No. 44, 1995, pp. 14441–14448.

Lewin, B., et al., "Cells Obey the Laws of Physics & Chemistry", *GENES V,* 1994, p. 13.

Bernstein, H., et al., *Methods in Enzymology,* (1988), 137:515–529.

Cardin, A., et al., *Arteriosclerosis,* (1989), 9:21–32.

Comfort, A., et al., *Biotech and Bioeng.,* (1989), 34:1383–1390.

Higuchi, R., et al., "PCR Protocols: A Guide to Methods and Applications", *Academic Press, Inc.* NY, (1990), 177–183.

Jackson, R., et al., *Physiol. Rev.* (1991), 71:481–539.

Kretsinger, R., et al., CRC Crit., Rev. Biochem., (1980), 8:119–174.

Leckband, D., et al., *Biotech Bioeng.,* (1991), 37:227–237.

Linhardt, R., et al., *Appl. Biochem. Biotechnol.* (1986), 12:135–176.

Linhardt, R., et al., *Biochemistry,* (1990), 29:2611–2617.

Lohse, D., et al., *J. Biol. Chem.,* (1992), 267:24347–24355.

Sasisekharan, R., et al., *Natl. Acad. Sci.,* (1993), 90:3660–3664.

Sasisekharan, R., et al., *Proc. Natl. Acad. Sci.,* (1994), 91:1524–1528.

Yang, V., et al., *J. Biol. Chem.,* (1985), 260:1849–1857.

SEQUENCE LISTING

<160> NUMBER OF SEQ ID NOS: 38

<210> SEQ ID NO 1
<211> LENGTH: 1379
<212> TYPE: DNA
<213> ORGANISM: Flavobacterium Heparinum
<220> FEATURE:
<221> NAME/KEY: CDS
<222> LOCATION: (173)...(1327)
<221> NAME/KEY: mat_peptide
<222> LOCATION: (236)...(1324)

<400> SEQUENCE: 1

```
cctttggga gcaaaggcag aaccatctcc gaacaaaggc agaaccagcc tgtaaacaga      60
cagcaattca tccgctttca accaaagtga aagcatttaa tacaatacca gaatgtcgca     120 tttcccttc agcgtacttt ttgggtaaat aaccaataaa actaaagac gg atg aaa      178
                                                        Met Lys
                                                          1
```

| | | | | | | | | | | | | | | | |
|---|---|---|---|---|---|---|---|---|---|---|---|---|---|---|---|
| aaa | caa | att | cta | tat | ctg | att | gta | ctt | cag | caa | ctg | ttc | ctc | tgt | tcg | 226 |
| Lys | Gln | Ile | Leu | Tyr | Leu | Ile | Val | Leu | Gln | Gln | Leu | Phe | Leu | Cys | Ser | |
| | 5 | | | | 10 | | | | | 15 | | | | | | |

```
gct tac gcc cag caa aaa aaa tcc ggt aac atc cct tac cgg gta aat      274
Ala Tyr Ala Gln Gln Lys Lys Ser Gly Asn Ile Pro Tyr Arg Val Asn
        20                  25                  30 gtg cag gcc gac agt gct aag cag aag gcg att att gac aac aaa tgg      322
Val Gln Ala Asp Ser Ala Lys Gln Lys Ala Ile Ile Asp Asn Lys Trp
 35                  40                  45                  50 gtg gca gta ggc atc aat aaa cct tat gca tta caa tat gac gat aaa      370
Val Ala Val Gly Ile Asn Lys Pro Tyr Ala Leu Gln Tyr Asp Asp Lys
                 55                  60                  65 ctg cgc ttt aat gga aaa cca tcc tat cgc ttt gag ctt aaa gcc gaa      418
Leu Arg Phe Asn Gly Lys Pro Ser Tyr Arg Phe Glu Leu Lys Ala Glu
             70                  75                  80 gac aat tcg ctt gaa ggt tat gct gca gga gaa aca aag ggc cgt aca      466
Asp Asn Ser Leu Glu Gly Tyr Ala Ala Gly Glu Thr Lys Gly Arg Thr
         85                  90                  95 gaa ttg tcg tac agc tat gca acc acc aat gat ttt aag aaa ttt ccc      514
Glu Leu Ser Tyr Ser Tyr Ala Thr Thr Asn Asp Phe Lys Lys Phe Pro
    100                 105                 110 cca agc gta tac caa aat gcg caa aag cta aaa acc gtt tat cat tac      562
Pro Ser Val Tyr Gln Asn Ala Gln Lys Leu Lys Thr Val Tyr His Tyr
115                 120                 125                 130 ggc aaa ggg att tgt gaa cag ggg agc tcc cgc agc tat acc ttt tca      610
Gly Lys Gly Ile Cys Glu Gln Gly Ser Ser Arg Ser Tyr Thr Phe Ser
                135                 140                 145 gtg tac ata ccc tcc tcc ttc ccc gac aat gcg act act att ttt gcc      658
Val Tyr Ile Pro Ser Ser Phe Pro Asp Asn Ala Thr Thr Ile Phe Ala
            150                 155                 160 caa tgg cat ggt gca ccc agc aga acg ctt gta gct aca cca gag gga      706
Gln Trp His Gly Ala Pro Ser Arg Thr Leu Val Ala Thr Pro Glu Gly
        165                 170                 175 gaa att aaa aca ctg agc ata gaa gag ttt ttg gcc tta tac gac cgc      754
Glu Ile Lys Thr Leu Ser Ile Glu Glu Phe Leu Ala Leu Tyr Asp Arg
    180                 185                 190 atg atc ttc aaa aaa aat atc gcc cat gat aaa gtt gaa aaa aaa gat      802
Met Ile Phe Lys Lys Asn Ile Ala His Asp Lys Val Glu Lys Lys Asp
195                 200                 205                 210
```

```
aag gac gga aaa att act tat gta gcc gga aag cca aat ggc tgg aag      850
Lys Asp Gly Lys Ile Thr Tyr Val Ala Gly Lys Pro Asn Gly Trp Lys
            215                 220                 225 gta gaa caa ggt ggt tat ccc acg ctg gcc ttt ggt ttt tct aaa ggg      898
Val Glu Gln Gly Gly Tyr Pro Thr Leu Ala Phe Gly Phe Ser Lys Gly
        230                 235                 240 tat ttt tac atc aag gca aac tcc gac cgg cag tgg ctt acc gac aaa      946
Tyr Phe Tyr Ile Lys Ala Asn Ser Asp Arg Gln Trp Leu Thr Asp Lys
            245                 250                 255 gcc gac cgt aac aat gcc aat ccc gag aat agt gaa gta atg aag ccc      994
Ala Asp Arg Asn Asn Ala Asn Pro Glu Asn Ser Glu Val Met Lys Pro
        260                 265                 270 tat tcc tcg gaa tac aaa act tca acc att gcc tat aaa atg ccc ttt     1042
Tyr Ser Ser Glu Tyr Lys Thr Ser Thr Ile Ala Tyr Lys Met Pro Phe
275                 280                 285                 290 gcc cag ttc cct aaa gat tgc tgg att act ttt gat gtc gcc ata gac     1090
Ala Gln Phe Pro Lys Asp Cys Trp Ile Thr Phe Asp Val Ala Ile Asp
            295                 300                 305 tgg acg aaa tat gga aaa gag gcc aat aca att ttg aaa ccc ggt aag     1138
Trp Thr Lys Tyr Gly Lys Glu Ala Asn Thr Ile Leu Lys Pro Gly Lys
        310                 315                 320 ctg gat gtg atg atg act tat acc aag aat aag aaa cca caa aaa gcg     1186
Leu Asp Val Met Met Thr Tyr Thr Lys Asn Lys Lys Pro Gln Lys Ala
            325                 330                 335 cat atc gta aac cag cag gaa atc ctg atc gga cgt aac gat gac gat     1234
His Ile Val Asn Gln Gln Glu Ile Leu Ile Gly Arg Asn Asp Asp Asp
        340                 345                 350 ggc tat tac ttc aaa ttt gga att tac agg gtc ggt aac agc acg gtc     1282
Gly Tyr Tyr Phe Lys Phe Gly Ile Tyr Arg Val Gly Asn Ser Thr Val
355                 360                 365                 370 ccg gtt act tat aac ctg agc ggg tac agc gaa act gcc aga tag         1327
Pro Val Thr Tyr Asn Leu Ser Gly Tyr Ser Glu Thr Ala Arg
            375                 380 caaaagccct aagcgcatcc gatagggctt ttcttatatt tacaataaaa tt           1379

<210> SEQ ID NO 2
<211> LENGTH: 384
<212> TYPE: PRT
<213> ORGANISM: Flavobacterium Heparinum

<400> SEQUENCE: 2

Met Lys Lys Gln Ile Leu Tyr Leu Ile Val Leu Gln Gln Leu Phe Leu
1               5                   10                  15

Cys Ser Ala Tyr Ala Gln Gln Lys Ser Gly Asn Ile Pro Tyr Arg
            20                  25                  30

Val Asn Val Gln Ala Asp Ser Ala Lys Gln Lys Ala Ile Ile Asp Asn
        35                  40                  45

Lys Trp Val Ala Val Gly Ile Asn Lys Pro Tyr Ala Leu Gln Tyr Asp
    50                  55                  60

Asp Lys Leu Arg Phe Asn Gly Lys Pro Ser Tyr Arg Phe Glu Leu Lys
65                  70                  75                  80

Ala Glu Asp Asn Ser Leu Glu Gly Tyr Ala Ala Gly Glu Thr Lys Gly
                85                  90                  95

Arg Thr Glu Leu Ser Tyr Ser Tyr Ala Thr Thr Asn Asp Phe Lys Lys
            100                 105                 110

Phe Pro Pro Ser Val Tyr Gln Asn Ala Gln Lys Leu Lys Thr Val Tyr
        115                 120                 125
```

His Tyr Gly Lys Gly Ile Cys Glu Gln Gly Ser Ser Arg Ser Tyr Thr
    130                 135                 140

Phe Ser Val Tyr Ile Pro Ser Ser Phe Pro Asp Asn Ala Thr Thr Ile
145                 150                 155                 160

Phe Ala Gln Trp His Gly Ala Pro Ser Arg Thr Leu Val Ala Thr Pro
                165                 170                 175

Glu Gly Glu Ile Lys Thr Leu Ser Ile Glu Gly Phe Leu Ala Leu Tyr
            180                 185                 190

Asp Arg Met Ile Phe Lys Lys Asn Ile Ala His Asp Lys Val Glu Lys
        195                 200                 205

Lys Asp Lys Asp Gly Lys Ile Thr Tyr Val Ala Gly Lys Pro Asn Gly
    210                 215                 220

Trp Lys Val Glu Gln Gly Gly Tyr Pro Thr Leu Ala Phe Gly Phe Ser
225                 230                 235                 240

Lys Gly Tyr Phe Tyr Ile Lys Ala Asn Ser Asp Arg Gln Trp Leu Thr
                245                 250                 255

Asp Lys Ala Asp Arg Asn Asn Ala Asn Pro Glu Asn Ser Glu Val Met
            260                 265                 270

Lys Pro Tyr Ser Ser Glu Tyr Lys Thr Ser Thr Ile Ala Tyr Lys Met
        275                 280                 285

Pro Phe Ala Gln Phe Pro Lys Asp Cys Trp Ile Thr Phe Asp Val Ala
    290                 295                 300

Ile Asp Trp Thr Lys Tyr Gly Lys Glu Ala Asn Thr Ile Leu Lys Pro
305                 310                 315                 320

Gly Lys Leu Asp Val Met Met Thr Tyr Thr Lys Asn Lys Lys Pro Gln
                325                 330                 335

Lys Ala His Ile Val Asn Gln Gln Glu Ile Leu Ile Gly Arg Asn Asp
            340                 345                 350

Asp Asp Gly Tyr Tyr Phe Lys Phe Gly Ile Tyr Arg Val Gly Asn Ser
        355                 360                 365

Thr Val Pro Val Thr Tyr Asn Leu Ser Gly Tyr Ser Glu Thr Ala Arg
    370                 375                 380

```
<210> SEQ ID NO 3
<211> LENGTH: 9
<212> TYPE: PRT
<213> ORGANISM: Flavobacterium Heparinum
<220> FEATURE:
<221> NAME/KEY: VARIANT
<222> LOCATION: (2)...(3)
<223> OTHER INFORMATION: Xaa is a basic residue.
<220> FEATURE:
<221> NAME/KEY: VARIANT
<222> LOCATION: (7)...(7)
<223> OTHER INFORMATION: Xaa is a basic residue.
<220> FEATURE:
<221> NAME/KEY: VARIANT
<222> LOCATION: (9)...(9)
<223> OTHER INFORMATION: Xaa is a basic residue.
<220> FEATURE:
<221> NAME/KEY: VARIANT
<222> LOCATION: (1)...(1)
<223> OTHER INFORMATION: Xaa is a hydrophobic or other residue.
<220> FEATURE:
<221> NAME/KEY: VARIANT
<222> LOCATION: (4)...(6)
<223> OTHER INFORMATION: Xaa is a hydrophobic or other residue.
<220> FEATURE:
<221> NAME/KEY: VARIANT
<222> LOCATION: (8)...(8)
<223> OTHER INFORMATION: Xaa is a hydrophobic or other residue.
```

```
<400> SEQUENCE: 3

Xaa Xaa Xaa Xaa Xaa Xaa Xaa Xaa Xaa
 1               5

<210> SEQ ID NO 4
<211> LENGTH: 8
<212> TYPE: PRT
<213> ORGANISM: Homo Sapiens
<220> FEATURE:
<221> NAME/KEY: VARIANT
<222> LOCATION: (2)...(4)
<223> OTHER INFORMATION: Xaa is a basic residue.
<220> FEATURE:
<221> NAME/KEY: VARIANT
<222> LOCATION: (7)...(7)
<223> OTHER INFORMATION: Xaa is a basic residue.
<220> FEATURE:
<221> NAME/KEY: VARIANT
<222> LOCATION: (1)...(1)
<223> OTHER INFORMATION: Xaa is a hydrophobic or other residue.
<220> FEATURE:
<221> NAME/KEY: VARIANT
<222> LOCATION: (5)...(6)
<223> OTHER INFORMATION: Xaa is a hydrophobic or other residue.
<220> FEATURE:
<221> NAME/KEY: VARIANT
<222> LOCATION: (8)...(8)
<223> OTHER INFORMATION: Xaa is a hydrophobic or other residue.

<400> SEQUENCE: 4

Xaa Xaa Xaa Xaa Xaa Xaa Xaa Xaa
 1               5

<210> SEQ ID NO 5
<211> LENGTH: 6
<212> TYPE: PRT
<213> ORGANISM: Homo Sapiens
<220> FEATURE:
<221> NAME/KEY: VARIANT
<222> LOCATION: (1)...(1)
<223> OTHER INFORMATION: Xaa is a hydrophobic or other residue.
<220> FEATURE:
<221> NAME/KEY: VARIANT
<222> LOCATION: (2)...(3)
<223> OTHER INFORMATION: Xaa is a basic residue.
<220> FEATURE:
<221> NAME/KEY: VARIANT
<222> LOCATION: (4)...(4)
<223> OTHER INFORMATION: Xaa is a hydrophobic or other residue.
<220> FEATURE:
<221> NAME/KEY: VARIANT
<222> LOCATION: (5)...(5)
<223> OTHER INFORMATION: Xaa is a basic residue.
<220> FEATURE:
<221> NAME/KEY: VARIANT
<222> LOCATION: (6)...(6)
<223> OTHER INFORMATION: Xaa is a hydrophobic or other residue.

<400> SEQUENCE: 5

Xaa Xaa Xaa Xaa Xaa Xaa
 1               5

<210> SEQ ID NO 6
<211> LENGTH: 10
<212> TYPE: PRT
<213> ORGANISM: Flavobacterium Heparinum

<400> SEQUENCE: 6

Lys Gly Ile Cys Glu Gln Gly Ser Ser Arg
 1               5                  10
```

```
<210> SEQ ID NO 7
<211> LENGTH: 24
<212> TYPE: PRT
<213> ORGANISM: Flavobacterium Heparinum

<400> SEQUENCE: 7
```

Lys Met Pro Phe Ala Gln Phe Pro Lys Asp Ile Cys Trp Ile Thr Phe
1               5                   10                  15

Asp Val Ala Ile Asp Trp Thr Lys
            20

```
<210> SEQ ID NO 8
<211> LENGTH: 16
<212> TYPE: PRT
<213> ORGANISM: Flavobacterium Heparinum

<400> SEQUENCE: 8
```

Lys Asp Ile Cys Trp Ile Thr Phe Asp Val Ala Ile Asp Trp Thr Lys
1               5                   10                  15

```
<210> SEQ ID NO 9
<211> LENGTH: 15
<212> TYPE: PRT
<213> ORGANISM: Flavobacterium Heparinum

<400> SEQUENCE: 9
```

Val Glu Lys Lys Asp Lys Asp Gly Lys Ile Thr Tyr Val Ala Gly
1               5                   10                  15

```
<210> SEQ ID NO 10
<211> LENGTH: 5
<212> TYPE: PRT
<213> ORGANISM: Flavobacterium Heparinum

<400> SEQUENCE: 10
```

Ser Gly Asn Ile Pro
1               5

```
<210> SEQ ID NO 11
<211> LENGTH: 4
<212> TYPE: PRT
<213> ORGANISM: Flavobacterium Heparinum

<400> SEQUENCE: 11
```

Val Gln Ala Asp
1

```
<210> SEQ ID NO 12
<211> LENGTH: 4
<212> TYPE: PRT
<213> ORGANISM: Flavobacterium Heparinum

<400> SEQUENCE: 12
```

Asn Lys Trp Val
1

```
<210> SEQ ID NO 13
<211> LENGTH: 4
<212> TYPE: PRT
<213> ORGANISM: Flavobacterium Heparinum

<400> SEQUENCE: 13
```

Val Gly Ile Asn
1

<210> SEQ ID NO 14
<211> LENGTH: 4
<212> TYPE: PRT
<213> ORGANISM: Flavobacterium Heparinum

<400> SEQUENCE: 14

Leu Arg Phe Asn
 1

<210> SEQ ID NO 15
<211> LENGTH: 4
<212> TYPE: PRT
<213> ORGANISM: Flavobacterium Heparinum

<400> SEQUENCE: 15

Thr Asn Asp Phe
 1

<210> SEQ ID NO 16
<211> LENGTH: 4
<212> TYPE: PRT
<213> ORGANISM: Flavobacterium Heparinum

<400> SEQUENCE: 16

Tyr His Tyr Gly
 1

<210> SEQ ID NO 17
<211> LENGTH: 4
<212> TYPE: PRT
<213> ORGANISM: Flavobacterium Heparinum

<400> SEQUENCE: 17

Ser Arg Ser Tyr
 1

<210> SEQ ID NO 18
<211> LENGTH: 4
<212> TYPE: PRT
<213> ORGANISM: Flavobacterium Heparinum

<400> SEQUENCE: 18

Trp His Gly Ala
 1

<210> SEQ ID NO 19
<211> LENGTH: 5
<212> TYPE: PRT
<213> ORGANISM: Flavobacterium Heparinum

<400> SEQUENCE: 19

Thr Leu Val Ala Thr
 1               5

<210> SEQ ID NO 20
<211> LENGTH: 4
<212> TYPE: PRT
<213> ORGANISM: Flavobacterium Heparinum

<400> SEQUENCE: 20

Lys Thr Leu Ser
 1

<210> SEQ ID NO 21
<211> LENGTH: 4

```
<212> TYPE: PRT
<213> ORGANISM: Flavobacterium Heparinum

<400> SEQUENCE: 21

Ile Thr Tyr Val
 1

<210> SEQ ID NO 22
<211> LENGTH: 5
<212> TYPE: PRT
<213> ORGANISM: Flavobacterium Heparinum

<400> SEQUENCE: 22

Thr Leu Ala Phe Gly
 1               5

<210> SEQ ID NO 23
<211> LENGTH: 5
<212> TYPE: PRT
<213> ORGANISM: Flavobacterium Heparinum

<400> SEQUENCE: 23

Tyr Phe Tyr Ile Lys
 1               5

<210> SEQ ID NO 24
<211> LENGTH: 4
<212> TYPE: PRT
<213> ORGANISM: Flavobacterium Heparinum

<400> SEQUENCE: 24

Arg Asn Asn Ala
 1

<210> SEQ ID NO 25
<211> LENGTH: 4
<212> TYPE: PRT
<213> ORGANISM: Flavobacterium Heparinum

<400> SEQUENCE: 25

Phe Asp Val Ala
 1

<210> SEQ ID NO 26
<211> LENGTH: 6
<212> TYPE: PRT
<213> ORGANISM: Flavobacterium Heparinum

<400> SEQUENCE: 26

Asp Val Met Met Thr Tyr
 1               5

<210> SEQ ID NO 27
<211> LENGTH: 4
<212> TYPE: PRT
<213> ORGANISM: Flavobacterium Heparinum

<400> SEQUENCE: 27

Ala His Ile Val
 1

<210> SEQ ID NO 28
<211> LENGTH: 10
<212> TYPE: PRT
<213> ORGANISM: Flavobacterium Heparinum
```

```
<220> FEATURE:
<221> NAME/KEY: VARIANT
<222> LOCATION: (1)...(1)
<223> OTHER INFORMATION: Xaa is lysine or arginine.

<400> SEQUENCE: 28

Xaa Gly Ile Cys Glu Gln Gly Ser Ser Arg
 1               5                  10

<210> SEQ ID NO 29
<211> LENGTH: 8
<212> TYPE: PRT
<213> ORGANISM: Flavobacterium Heparinum
<220> FEATURE:
<221> NAME/KEY: VARIANT
<222> LOCATION: (1)...(1)
<223> OTHER INFORMATION: Xaa is lysine or arginine.

<400> SEQUENCE: 29

Xaa Thr Val Tyr His Tyr Gly Lys
 1               5

<210> SEQ ID NO 30
<211> LENGTH: 8
<212> TYPE: PRT
<213> ORGANISM: Flavobacterium Heparinum
<220> FEATURE:
<221> NAME/KEY: VARIANT
<222> LOCATION: (1)...(1)
<223> OTHER INFORMATION: Xaa is lysine or arginine.

<400> SEQUENCE: 30

Xaa Thr Ser Thr Ile Ala Tyr Lys
 1               5

<210> SEQ ID NO 31
<211> LENGTH: 6
<212> TYPE: PRT
<213> ORGANISM: Flavobacterium Heparinum
<220> FEATURE:
<221> NAME/KEY: VARIANT
<222> LOCATION: (1)...(1)
<223> OTHER INFORMATION: Xaa is lysine or arginine.

<400> SEQUENCE: 31

Xaa Phe Gly Ile Tyr Arg
 1               5

<210> SEQ ID NO 32
<211> LENGTH: 22
<212> TYPE: PRT
<213> ORGANISM: Flavobacterium Heparinum
<220> FEATURE:
<221> NAME/KEY: VARIANT
<222> LOCATION: (1)...(1)
<223> OTHER INFORMATION: Xaa is lysine or arginine.
<220> FEATURE:
<221> NAME/KEY: UNSURE
<222> LOCATION: (17)...(17)
<223> OTHER INFORMATION: Xaa is any amino acid residue.

<400> SEQUENCE: 32

Xaa Ala Asp Ile Val Asn Gln Gln Glu Ile Leu Ile Gly Arg Asp Asp
 1               5                  10                  15

Xaa Gly Tyr Tyr Phe Lys
             20
```

```
<210> SEQ ID NO 33
<211> LENGTH: 25
<212> TYPE: PRT
<213> ORGANISM: Flavobacterium Heparinum
<220> FEATURE:
<221> NAME/KEY: VARIANT
<222> LOCATION: (1)...(1)
<223> OTHER INFORMATION: Xaa is lysine or arginine.
<220> FEATURE:
<221> NAME/KEY: UNSURE
<222> LOCATION: (25)...(25)
<223> OTHER INFORMATION: Xaa is any amino acid residue.

<400> SEQUENCE: 33

Xaa Ile Thr Tyr Val Ala Gly Lys Pro Asn Gly Asn Lys Val Glu Gln
 1               5                  10                  15

Gly Gly Tyr Pro Thr Leu Ala Phe Xaa
            20                  25

<210> SEQ ID NO 34
<211> LENGTH: 23
<212> TYPE: PRT
<213> ORGANISM: Flavobacterium Heparinum
<220> FEATURE:
<221> NAME/KEY: VARIANT
<222> LOCATION: (1)...(1)
<223> OTHER INFORMATION: Xaa is lysine or arginine.
<220> FEATURE:
<221> NAME/KEY: UNSURE
<222> LOCATION: (21)...(21)
<223> OTHER INFORMATION: Xaa is any amino acid residue.

<400> SEQUENCE: 34

Xaa Met Pro Phe Ala Gln Phe Pro Lys Asp Cys Trp Ile Thr Phe Asp
 1               5                  10                  15

Val Ala Ile Asp Xaa Thr Lys
            20

<210> SEQ ID NO 35
<211> LENGTH: 11
<212> TYPE: PRT
<213> ORGANISM: Flavobacterium Heparinum
<220> FEATURE:
<221> NAME/KEY: VARIANT
<222> LOCATION: (1)...(1)
<223> OTHER INFORMATION: Xaa is lysine or arginine.

<400> SEQUENCE: 35

Xaa Asn Leu Ser Gly Tyr Ser Glu Thr Ala Arg
 1               5                  10

<210> SEQ ID NO 36
<211> LENGTH: 11
<212> TYPE: PRT
<213> ORGANISM: Flavobacterium Heparinum

<400> SEQUENCE: 36

Lys Asn Ile Ala His Asp Lys Val Glu Lys Lys
 1               5                  10

<210> SEQ ID NO 37
<211> LENGTH: 14
<212> TYPE: PRT
<213> ORGANISM: Flavobacterium Heparinum

<400> SEQUENCE: 37

Lys Thr Leu Ser Ile Glu Glu Phe Leu Ala Leu Tyr Asp Arg
 1               5                  10
```

-continued

```
<210> SEQ ID NO 38
<211> LENGTH: 41
<212> TYPE: PRT
<213> ORGANISM: Flavobacterium Heparinum

<400> SEQUENCE: 38

Arg Ser Tyr Thr Phe Ser Val Tyr Ile Pro Ser Ser Phe Pro Asp Asn
1               5                   10                  15

Ala Thr Thr Ile Phe Ala Gln Trp His Gly Ala Pro Ser Arg Thr Leu
            20                  25                  30

Val Ala Thr Pro Glu Gly Glu Ile Lys
            35                  40
```

RATIONALLY DESIGNED POLYSACCHARIDE LYASES DERIVED FROM HEPARINASE I

This application claims benefits of provisional application Ser. No. 60/008,069 filed Oct. 30, 1995.

GOVERNMENT SUPPORT

The present invention was supported in part by a grant from the United States National Institutes of Health (GM 25810). The U.S. government retains certain rights in the invention.

FIELD OF THE INVENTION

The present invention relates to polysaccharide lyases and the rational design of the same. In particular, the present invention relates to new polysaccharide lyases rationally designed and based upon the heparinase I of *Flavobacterium heparinum*.

The polysaccharides heparin and heparin sulfate are characterized by a disaccharide repeating unit of uronic acid and hexosamine, where the uronic acid is either L-iduronic acid or D-glucuronic acid and the glucosamine is linked to the uronic acid by a 1→4 linkage (Jackson et al., 1991). Heparin-like molecules are complex due to the high degree and varying patterns of sulfation on both the uronic acid and the hexosamine residues. It is believed that it is the sulfation which is responsible for the numerous different functional roles of these carbohydrates. Our understanding of heparin's functional role is severely limited by our poor knowledge of the heparin sequence.

Heparinases have proved to be useful tools in heparin degradation and in providing composition and sequence information (Linhardt et al., 1990). *F. heparinum* produces at least three types of heparinases (I, II and III) with different substrate specificities (Lohse & Linhardt, 1992). It has been proposed that all three enzymes cleave heparin through an elimination reaction catalyzed by a nucleophilic amino acid.

Heparinase I (or heparin lyase I, EC 4.2.2.7) is a 42,500 Da enzyme isolated from the periplasm of *F. heparinum* which cleaves heparin specifically in a random endolytic fashion (Linker and Hoving, 1972; Linhardt et al., 1982) at linkages of the type $H_{NS,6X}I_{2S}$ or $H_{NS,6X}I_{2X}$, where X is either sulfated or unsubstituted (Linhardt, et al., 1990; Desai, et al., 1993). The characteristic heparin degradation product profile includes $\Delta U_{2S}H_{NS}$ (disaccharide 1); $\Delta U_{2S}H_{NS,6S}$ (disaccharide 2), $\Delta U_{2S}H_{NS}I_{2S}H_{NS,6S}$ (tetrasaccharide 1), $\Delta U_{2S}H_{NS,6S}GH_{NS,6S}$ (tetrasaccharide 2), $\Delta U_{2S}H_{NS,6S}I_{2S}H_{NS,6S}$ (tetrasaccharide 3), and $\Delta U_{2S}H_{NS,6S}IH_{NAc,6S}GH_{NS,3S,6S}$ (hexasaccharide).

Heparinase I has recently been cloned and expressed in *E. coli* (Sasisekharan et al., 1993). The enzyme has be utilized in the sequence determination of sugars, in the preparation of small heparin fragments for the therapeutic uses, and in the ex vivo removal of heparin from blood (Linhardt et al., 1990; Bernstein et al., 1988). Extracorporeal medical devices (e.g. hemodialyzer, pump-oxygenator) rely on systemic heparinization to provide blood compatibility within the device and a blood filter containing immobilized heparinase I at the effluent which is capable of neutralizing the heparin before the blood is returned to the body (Bernstein et al., 1988).

It has been suggested that heparinase I binds heparin through lysine residues on the enzyme surface (Yang et a., 1985; Linhardt et al., 1982). The importance of lysines in enzyme activity is suggested by the observation that modification by amine-reactive reagents and immobilization of heparinase I on amine-active supports result in extensive activity losses (Comfort et al., 1989; Leckband & Langer, 1991; Bernstein et al., 1988). Further evidence for an electrostatic nature of the interaction lies in the pH and ionic strength dependence of heparinase activity (Yang et al., 1985). Additionally, the finding that tetrasaccharides are the smallest heparin fragments that still retain substrate activity gives some information about the size requirements of the active site (Linhardt et al., 1990). Despite these observations, information concerning the structure of the enzyme has been scant.

There has been much speculation in the art about the possibility of creating "designer" enzymes, rationally designed to have desired substrate specificities and activities, and heparinase I would be an appropriate staring point for the rational design of novel polysaccharide lyases. Yet, although the importance of different levels (primary, secondary, and tertiary) of protein structure in determining the functional activity of enzymes has long; been recognized, the lack of a broad and detailed understanding of the relationship be structure and function has prevailed significant progress. Even for enzymes which have known activities, substrates, and primary structure, the general lack of information about secondary and tertiary structures and the relationship of these to function has made it difficult to predict the functional effect of any particular changes to the primary structure.

SUMMARY OF THE INVENTION

The present invention provides for new polysaccharide lyases derived from heparinase and rationally-designed based upon detailed structural and functional characterization of heparinase. In particular, in one series of embodiments, the present invention provides substantially pure polysaccharide lyases composing the amino acid sequence of the mature heparinase I protein of *F. heparinum* in which at least one amino acid residue has been substituted and in which the substitution is (a) a substitution of a cysteine residue corresponding to position 135 of SEQ ID NO: 2 with a residue selected from the group consisting of aspartate, glutamate, serine, threonine, and histidine; (b) a conservative substitution of a residue of a Cardin-Weintraub-like heparin-binding sequence XBBXXXBXB (SEQ ID NO: 3) corresponding to positions 197–205 or 208–212 of SEQ ID NO: 2 with a residue which conforms to the heparin-binding sequence; (c) a conservative substitution of a residue of an EF-hand-like calcium binding sequence corresponding to positions 206–220 of SEQ ID NO: 2 with a residue which conforms to the calcium binding sequence; (d) a conservative substitution of a residue of a PB1, PB2 or PB3 β-sheet domain of SEQ ID NO: 2; (e) a non-conservative substitution of a cysteine residue corresponding to position 297 of SEQ ID NO: 2; (f) a non-conservative substitution of a residue of a PB1, PB2 or PB3 β-sheet domain of SEQ ID NO: 2 which preserves a parallel β-helix tertiary structure characteristic of SEQ ID NO: 2;(g) a deletion of one or more residues of a N-terminal region or a C-terminal region of SEQ ID NO: 2 which preserves a parallel β-helix tertiary structure characteristic of SEQ ID NO: 2; or (h) a non-conservative substitution of a serine residue corresponding to position 39 of SEQ ID NO: 2.

The present invention thus contemplates any of the foregoing substitutions alone, but also contemplates combinations of these substitutions which result in functionally active modified heparinases with altered stability, activity, and/or specificity as described in greater detail below.

It is, for example, a particular object of the invention to provide substantially pure polysaccharide lyases based upon heparinase I in which the cysteine residue corresponding to position 135 of heparinase I has been substituted with an aspartate, glutamate, serine, threonine, or histidine.

It is, for example, another particular object of the invention to provide substantially pure polysaccharide lyases based upon heparinase I in which the serine residue corresponding to position 39 of heparinase I has been substituted with an alanine residue.

It is, for example, another particular object of the invention to provide substantially pure polysaccharide lyases based upon heparinase I in which a residue of a Cardin-Weintraub-like heparin binding sequence XBBXXXBXB corresponding to positions 197–205 or 208–212 of heparinase I has been conservatively substituted with a residue which conforms to the heparin binding sequence. In a preferred set of embodiments, the conservative substitution is of a lysine residue corresponding to position 198, 199 or 205 of heparinase I with an arginine or histidine, most preferably an arginine. In other preferred embodiments, the conservative substitution is of the histidine residue corresponding to position 203 of heparinase I.

It is, for example, yet another particular object of the invention to provide substantially pure polysaccharide lyases based upon heparinase I in which a consecutive substitution of a residue of an EF-hand-like calcium binding sequence corresponding to positions 206–220 of heparinase I with a residue which conforms to the calcium binding sequence has been made. In preferred embodiments, the substitution is of a lysine residue corresponding to position 208, 209, 211 or 214 of heparinase I with an arginine or histidine, preferably an arginine. In other preferred embodiments, the substitution is of an aspartate residue corresponding to positions 210 or 212 of heparinase I with a glutamate.

According to another aspect of the invention, there is provided a high order low molecular weight heparin fragments greater tan hexasaccharides obtainable by the process of incubating with heparin the substantially pure polysaccharide lyase of the invention (described above) to produce the low molecular weight heparin fragment. The low molecular weight heparin fragments can be separateded on an anionic exchange chromatography column (such as a POROS column from PerSeptive Biosystems).

According to another aspect of the invention, there is provided a pharmaceutical preparation comprising a sterile formulation of the substantially pure polysaccharide lyase of the invention (described above) and a pharmaceutically acceptable carrier.

According to another aspect of the invention, there is provided methods for treating subjects in need of depletion of circulating heparin. Effective amounts of the polysaccharides of the invention awe administered to subjects in need of such treatment According to another at of the invention there is provided an isolated nucleic acid encoding the substantially pure polysaccharide lyase of the invention. This aspect of the invention also includes nucleic acids which hybridize under stringent hybridization conditions to the isolated nucleic acid of SEQ ID NO 1 or to the complement of the nucleic acid of SEQ ID NO 1 and which are modified to encode a modified heparinase as described above, and nucleic acids that differ from the nucleic acids ub codon sequence due to the degeneracy of the genetic code.

The invention further provides a recombinant host cell including any of the isolated nucleic acids of the invention.

The invention further provides an expression vector including any of the isolated nucleic acids of the invention.

According to another aspect of the invention there is provided a method of removing active heparin from a heparin containing fluid. The method involves the step of contacting a heparin containing fluid with the substantially pure polysaccharide lyase of the invention. In one embodiment of the invention the substantially pure polysaccharide lyase is immobilize on a solid support.

In another series of embodiments, the present invention provides new polysaccharide lyases in which nonconsecutive substitutions have been made. Thus, these embodiments include substantially pure polysaccharide lyases based upon heparinase I in which at least one amino acid residue has been substituted and in which the substitution is (a) a substitution of a cysteine residue corresponding to position 135 of heparinase I with an aspartate, glutamate, serine, threonine or histidine residue; (b) a substitution of a histidine residue corresponding to position 203 of heparinase I with an aspartate, glutamate, serine, threonine or cysteine; (c) a substitution of a lysine residue corresponding to position 198, 199, 205, 208, 209, 211 or 214 of heparinase I with a small non-polar amino acid, a small polar amino acid, or an acidic amino acid; (d) a substitution of a small polar or small non-polar amino acid for a residue corresponding to the Phe197, Asn200, Asp204, Glu207, Asp210, Asp212 or Gly213 of heparinase I.

In this series of embodiments, the present invention provides for single substitutions and also provides for polysaccharide lyases with combinations of these substitutions as discussed above.

In another series of embodiments, the present invention provides for a modified heparinase having a modified heparinase $k_{cat}$ value, wherein the modified heparinase $k_{cat}$ value is $\leq 75\%$ of a native heparinase $k_{cat}$ value of a complementary native heparinase. The complementary native heparinase for modified heparinase I is, of course, heparinase I.

In another series of embodiments the modified heparinase is immobilized on a solid support membrane.

In another series of embodiments, the present invention also provides for polysaccharide lyases in which the overnight heparin degradation activity is less than about 75% of that of native heparinase I.

In another series of embodiments, the present invention also provides for polysaccharide lyases in which the degradation product profile is altered from that of native heparinase I. In one embodiment the polysaccharide lyase is a modified heparinase I having a modified product profile, wherein the modified product profile of the modified heparinase I is $\leq 50\%$ similar to a native product profile of a native heparinase I. In another embodiment the substantially pure polysaccharide lyase is a modified heparinase I producing when contacted with heparin less than 20% of disaccharide 1 and trisaccharides 2 and 3 as compared to native heparinase I when contacted with the heparin.

In another series of embodiments, the present invention also provides active fragments and functionally equivalent variants thereof of the polysaccharide lyases of the invention that have substantially the same heparinase I activity as the substituted polysaccharide lyases of the invention.

DETAILED DESCRIPTION OF THE INVENTION

Figure 1:
FIG. 1 presents a "side" view of the parallel β-sheet structure of the core of heparinase I in which Cys135 is marked by an arrow.

The present invention provides a series of new polysaccharide lyases derived from the heparinase I (heparin lyase 1, EC 4.22.7) of *F. heparinum*. In particular, based upon a detailed structural and functional characterization of heparinase I, new polysaccharide lyases with altered stability, activity and specificity are provided.

The nucleotide and amino acid sequences of heparinase I are provided in SEQ ID NO: 1 and SEQ ID NO: 2, respectively. These sequences were reported in Sasisekharan, et al. (1993) and provided the first insight into the primary structure of the native heparinase I of *F. heparinum*.

The present disclosure provides a wealth of additional information about the secondary and tertiary she of this polysaccharide lyase as well as information relating to the functional roles of the various regions of the enzyme. This information is based upon detailed biochemical mapping of the active site and polysaccharide binding domain, characterization of these sites through kinetic studies, characterization of mutants created by site-directed mutagenesis, and computer-based modeling of secondary and tertiary structures. The result is a detailed picture of the primary, secondary, and tertiary structures of heparinase I and the functional roles of various regions of the enzyme.

Using this detailed knowledge of the native heparinase I of *F. heparinum*, the present disclosure provides novel, rationally designed polysaccharide lyases, methods of designing and producing such lyases, and uses therefor.

Heparinase I has a typical prokaryotic leader sequence and cleavage site. This leader sequence corresponds to residues 1–21 of SEQ ID NO: 2. A recombinant construct lacking the leader (L) residues, designated -L r-heparinase I, has been expressed in a pET plasmid and the recombinant enzyme is still as active as the native *F. heparinum*, indicating that these residues are not essential for enzymatic activity. Inclusion of the leader in the mature protein, however, does not interfere with the enzyme's activity (Sasisekharan et al., 1993).

Although the full Base I amino acid sequence includes three cysteines, one of these Us (at position 17 of SEQ ID NO: 2) is in the leader sequence. Therefore, the mature heparinase I has two cysteines. These cysteines are at positions 135 ("Cys135") and 297 ("Cys297") of SEQ ID NO: 2.

Previous studies had suggested that the two cysteine residues of mature heparinase I form a disulfide bridge. Comfort et al. (1989), for example, compared the activity of heparinase I in which the cysteine residues had been reduced with heparinase in which the cysteines had not been altered. These experiments showed that the reduced heparinase I had lower activity than the native heparinase I. Therefore, it was suggested that the two cysteine residues may form a disulfide bridge in native heparinase I and that the disulfide bridge may be important to maintaining tertiary structure and activity.

Studies using sulfhydryl modifications, kinetics of enzyme inactivation, and competitive inhibition of inactivation were performed by the pent inventors to determine the functional roles of the two cysteines in catalysis. Purified heparinase I preparations (Example 1) were modified with various sulfhydryl specific reagents to map and characterize the cysteine residues.

We now disclose (a) that the two cysteines of heparinase I do not form a disulfide bridge but, rather, are located in different parts of the tertiary structure with different microenviromnents, (b) that Cys135 is surface-accessible, (c) that Cys135 is in the active site, (d) that the microenvironment around Cys135 is positively charged, and (e) that Cys135 is involved in catalysis. In contrast, Cys297 is buried in the hydrophobic core of the protein and is not essential to heparinase I activity. See Examples 2–8.

To further demonstrate that Cys135 is an active site cysteine involved in catalysis and that Cys297 is not essential to enzyme activity, recombinant polysaccharide lyases were produced in which these residues were modified. Using site-directed mutagenesis, Cys135 was replaced by the more weakly nucleophilic residue serine, by the charged residues histidine, glutamate and aspartate, and by the neutral alanine. Replacement of Cys135 by aspartate, glutamate, serine or histidine led to decreases in activity ($k_{cat}$ values of approximately 3.5%, 3.8%, 2% and 3%, respectively, of the I of native heparinase) and replacement with the neutral alanine abolished activity. Importantly, the cleavage specificity of the recombinant lyases was unaffected. Replacement of Cys297 with either serine or alanine had no effect on activity. See Example 9.

Next, we investigated the heparin-binding domain of heparin I using activity analysis at varying calcium concentrations, heparin affinity chromatography, affinity co-electrophoresis, heparin blotting of CnBr digests, competitive binding and blotting of tryptic digests, competition with a synthetic binding domain peptide, PCMB protection and tryptic digests, and site-directed mutagenesis of the binding domain See Examples 10–17.

We now disclose that (a) heparinase I possesses a lysine-rich heparin binding domain extending approximately from residues 195–220 of SEQ ID NO.:2, (b) that the binding domain possesses two "Cardin-Weintraub" heparin binding sequences at approximately residues 197–205 and 206–212, (c) that heparinase activity is calcium dependent and the heparin binding domain contains an EF-hand-like calcium binding site at approximately residues 206–220, and (d) that the heparin binding domain is in close proximity to Cys135 in native heparinase I.

As noted above, the heparin binding domain possesses two sequences which almost conform to consensus sequences found in many heparin binding proteins (Cardin and Weintraub, 1989). The Cardin-Weintraub sequence is of the form XBBBXXBX or XBBXBX (where B is any basic residue and X is any hydrophobic or other residue). The heparinase I sequences which nearly conform to these sequences are found at positions 197–205 and 206–212 of SEQ ID NO.:2. Using site-directed mutagenesis, recombinant proteins were produced in which these sites were altered. A third Cardin-Weintraub sequence, at approximately positions 331–337, does not appear to be involved in heparin binding.

Also within the heparin binding domain is a sequence which nearly conforms to an EF-hand calcium binding domain (Kretsinger et al., 1991) at positions 206–220. The EF-hand consensus sequence is shown in Table II. Substitutions conforming to an EF-hand calcium binding consensus sequence, but which would not conform to a Cardin- Weintraub heparin binding sequence, appear to be tolerated but a deletion of the entire sequence leads to enzyme inactivity. For example, substitution of both Lys208 and Lys209 with the similarly positive arginine led to a 40% decrease in initial activity ($k_{cat}$) but had no effect on the product profile. This substitution is consistent with both the EF-hand and Cardin-Weintraub consensus sequences. Substitution of both of these residues with the neutral alanine did not significantly alter the product profile but led to a 76% decrease in $k_{cat}$. This substitution conforms to the EF-hand consensus but not the Cardin-Weintraub consensus. Moreover, substitution of both lysines with negative aspartate residues results in a decease in $k_{cat}$ of only 46% and an unaltered product profile, further showing that the amines of these lysine residues are not necessary for catalysis. Therefore this stretch of the sequence is primarily a calcium binding site and, secondarily, a heparin binding sequence. Deletion of this region abolishes activity, suggesting either that calcium is necessary to activity or that the deletion disrupts the tertiary structure of the active site. A second EF-hand domain, at approximately positions 372–384, does not appear to be involved in catalysis.

With respect to the heparin binding site at residues 197–205, a different picture emerges. This sequence nearly conforms to a Cardin-Weintraub heparin binding sequence, having the motif XBBXXXBXB. This sequence does not conform to an EF-hand calcium binding site. Substitution of positively charged arginines for lysines (Lys198 and Lys199) conserves the Cardin-Weintraub-like motif and results in a 46% decrease in $k_{cat}$ but no change in product profile. Interestingly, substitution of Lys198 and Lys199 with either the neutral alanine or negatively charged aspartate does not abolish activity but, rather, results in lower activity ($k_{cat}$ 4.1% of wild type) and an altered product profile. Another basic residue in this domain, His203, appears to be involved in the active site as an acid/base catalyst Substitution of His203 with nucleophilic negative or polar residues which do not conform to the Cardin-Weintraub sequence (e.g., aspartate, serine or cysteine) does not inactivate the enzyme but, rather, results in a lyase with decreased activity ($k_{cat}$ 3–4% of wild type). Substitution with the neutral alanine, however, abolishes activity, suggesting that this residue may be important in proton transfer.

Using the information relating to the active site and heparin binding domain of heparinase I, in conjunction with computer database searches for homologous sequences of known structure, computer programs for the prediction of secondary structures, and computer-assisted modeling, we have developed a model of the tertiary structure of native heparinase I.

Figure 2:
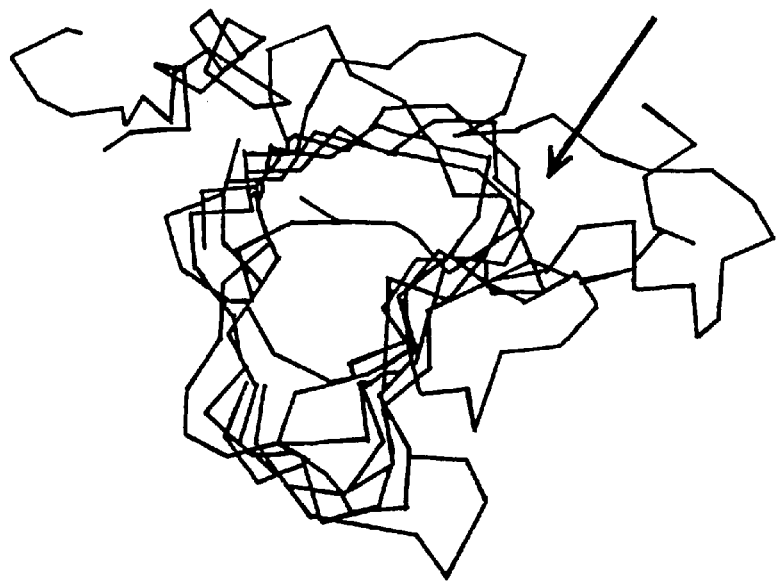
FIG. 2 presents a view "down" the axis of the parallel β-helix of the core of heparinase I in which Cys135 is marked by an arrow.

We now disclose that heparinase I is characterized by a parallel β-helix structure. A similar structure has recently been reported for two pectate lyases (Yoder et al., 1993). For much of this structure, each turn of the helix consists of two or three β-strands separated by non-β stretches. The tuns of the helix are stacked such that the β-strands of adjacent turns may form parallel β-sheets. Thus, the helix is three-sided for most of the core structure with the three sides consisting largely of three parallel β-sheets. The three parallel β-sheets forming the sides of the helical core are designated PB1, PB2, PB3. In each turn, the 0-stands are between two and seven residues in length and each turn includes a minimum of seventeen residues and an average of about nine residues in β-stands. Between β-strands are loops of varying lengths. Both Cys135 and the heparin binding domain are found in such loops. Table I discloses the approximate positions of the residues of heparinase I which are found in the β-strands and to which of the β-sheets each β-strand belongs. Schematic views of the scaffold of Table I, omitting some of loops between β-strands, are presented in FIGS. 1 and 2. FIG. 1 presents a "side" view in Which Cys135 is marked by an arrow. FIG. 2 presents a view "down" the axis of the parallel β-helix and, again, Cys135 is marked by an arrow.

Note that the active site cysteine, Cys135, is located in a non-β-stretch between PB1 and PB2. This is consistent with the results of the sulfhydryl modification experiments which indicated that Cys135 is surface accessible. Cys297, on the other hand, is part of a β-strand in PB1 and its side chain is believed to be directed toward the hydrophobic interior of the helix. The heparin binding domain loops out of a turn between PB3 and PB1 and extends back up the β-helix toward Cys135. This structure places the active site cysteine in proximity to the heparin binding domain and explains the positively charged microenvironment of Cys135 and the inhibition of the PCMB reaction with Cys135 by the addition of heparin.

From the results disclosed herein, a molecular mechanism for the interplay between heparin binding and catalysis by heparinase I emerges. Cys135 is catalytically active, but is not a determinant for heparin binding, since chemically derivatizing it did not affect heparinase binding to heparin. It is proposed that this residue abstracts the C5 proton on the uronate of the disaccharide repeat unit of the acidic polysaccharides, and initiates the elimination based depolymerization reaction. The thiol group of cysteine has a $pK_a$ of 8.35 in free solution (Fresht, 1985), indicating that this residue will be filly protonated at pH 7.0, the pH optimum for heparinase I (Yang et al., 1985). A positively charged environment from nearby lysines or arginines, however, will tend to keep the thiol group negatively charged (i.e. lowering its $pK_a$) so that it can act as a base for proton abstraction. This would account for the preferential reactivity of Cys135 with negatively charged reagents and the high reactivity of Cys135 at pH 6.5 (Example 6).

Figure 3:
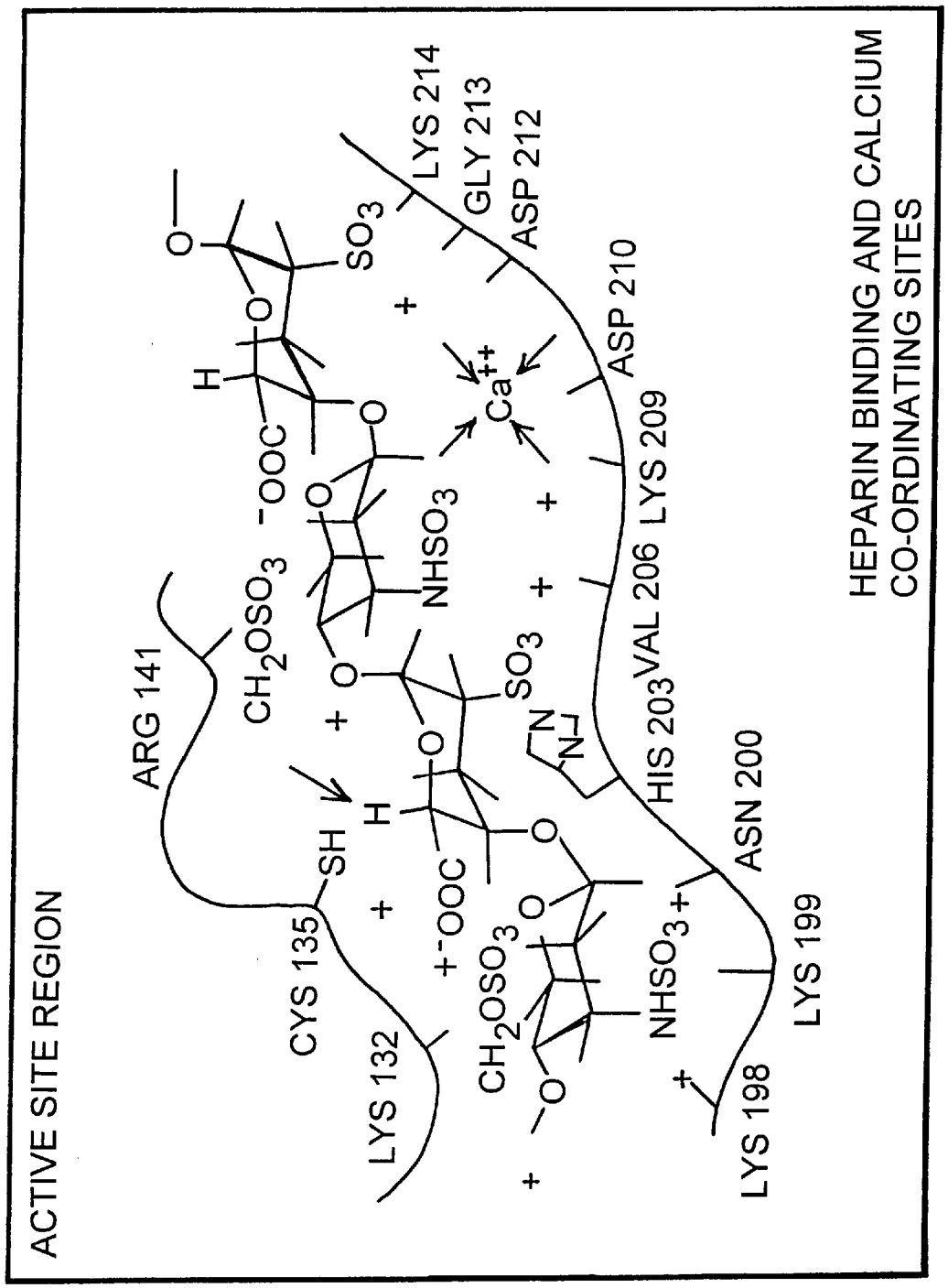
FIG. 3 shows a heparin tetrasaccharide bound in the heparin binding domain Cys135 and His203 are in close proximity to each other and the hydrogen of the iduronate marked by an arrow.

The heparin binding domain (residues 195–220) controls enzymatic selectivity in terms of substrate size, and the histidine from this region (His203) also assists the catalytic mechanism, possibly by acting as a secondary nucleophile or as an essential amino acid in a possible "proton relay system." This site also contains the calcium co-ordination site which bridges heparin to heparinase through calcium, and perhaps orients the functional group(s) of the uronate to the active site region involving Cys135 and His203. The heparin binding site and the basic residues close to Cys135 (e.g., Lys132, Arg141, etc.) together constitute a heparin binding domain in heparinase I that provide the basic environment for Cys135. Substitution of ILysine132 to an alanine residue reduced the activity of the heparinase (see table IV). This positive charge environment around the surface accessible Cys135 enhances the reactivity of this thiol residue. Thus, we postulate that a positively charged heparin binding domain spatially close to Cys135 provides the necessary charge complementarity for very specific heparin binding on the one hand, while on the other it provides for the active site environment which plays a key role in biasing the active site reactivity. FIG. 3 shows a schematic representation of the active site of heparinase I with a heparin tetrasaccharide bound in the heparin binding domain. Cys135 and His203 are in close proximity to each other and to the hydrogen of the iduronate marked by an arrow.

In light of the present disclosure, one of ordinary skill in the art is now able to rationally design new polysaccharide lyases with altered activity and specificity. In particular, one is able to design lyases with altered activity by the modification of Cys135 or the positively charged residues surrounding it in the active site or the heparin binding domain. In addition, one is enabled to design modified polysaccharide lyases with altered specificity by modification of the residues of the Cardin-Weintraub-like sequence in the heparin binding domain. Finally, one is able to produce various other novel polysaccharide lyases in which non essential residues are freely changed or substituted conservatively.

PREFERRED EMBODIMENTS

The present invention provides for novel polysaccharide lyases rationally designed on the basis of the sequence of the heparinase I of *F. heparinum* and the structural and functional characterizations disclosed herein.

In the description that follows, reference will be made to the amino acid residues and residue positions of native heparin I disclosed in SEQ ID NO: 2. In particular, residues and residue positions will be referred to as "corresponding to" a particular residue or residue position of heparin I. As will be obvious to one of ordinary skill in the art, these positions are relative and, therefore, insertions or deletions of one or more residues would have the effect of altering the numbering of downstream residues. In particular, N-terminal insertions or deletions (e.g., deletion of one or more of the 21 N-terminal leader sequence residues) would alter the numbering of all subsequent residues. Therefore, as used herein, a residue in a recombinant polysaccharide lyase will be referred to as "corresponding to" a residue of the full heparinase I if, using standard sequence comparison programs, they would be aligned Many such sequence alignment programs are now available to one of ordinary skill in the art and their use in sequence comparisons has become standard (e.g., "LALIGN" available via the internet at http://genome.eerie.fr/fasta/). As used herein, this convention of referring to the positions of residues of the recombinant polysaccharide lyases by their corresponding heparinase I residues shall extend not only to embodiments including N-terminal insertions or deletions but also to internal insertions or deletions (e.g, insertions or deletions in "loop" regions).

In addition, in the description which follows, certain substitutions of one amino acid residue for another in a recombinant polysaccharide lyase will be referred to as "conservative substitutions." As used herein, a "conservative amino acid substitution" or "conservative substitution" refers to an amino acid substitution in which the substituted amino acid residue is of similar charge as the replaced residue and is of similar or smaller size than the replaced residue. Conservative substitutions of amino acids include substitutions made amongst amino acids within the following groups: (a) the small non-polar amino acids, A, M, I, L, and V; (b) the small polar amino acids, G, S, T and C; (c) the amido amino acids, Q and N; (d) the aromatic amino acids, F, Y and W; (e) the basic amino acid, K, R and H; and (0) the acidic amino acids, E and D. Substitutions which are charge neutral and which replace a residue with a smaller residue may also be considered "conservative substitutions" even if the residues are in different groups (e.g., replacement of phenylalanine with the smaller isoleucine).

Additionally, some of the amino acid substitutions are non-conservative substitutions. In certain embodiments where the substitution is remote from the active or binding sites, the non-conservative substitutions are easily tolerated provided that they preserve the parallel B-helix tertiary structure characteristic of native heparinase (SEQ ID NO: 2), thereby preserving the active and binding sites.

As shown in the experimental examples below and, in particular Table IV, the present invention provides a variety of novel polysaccharide lyases with heparin-cleaving activity in which the initial activity or $k_{cat}$ is reduced relative to the $k_{cat}$ of native heparinase I. For each of the novel polysaccharide lyases tested thus far, the $k_{cat}$ of the recombinant lyase is less than about 75% of that of native heparinase I. Such lyases have particular utility as substitutes for heparinase I in the controlled degradation of heparin and other polysaccharides because the reaction proceeds at a slower rate. Table IV also shows the percentage of degradation products, relative to native heparinase I, produced by these new lyases after overnight incubation with heparin. In all cases but two, discussed below, the product profile of these new lyases is essentially identical to the characteristic heparinase I product profile.

The novel polysaccharide lyases of the invention are rationally designed based upon the sequence of heparinase I and have at least one amino acid substitution at the active site Cys135, in the first Cardin-Weintaub-like sequence in the heparin binding domain, or in the EF-hand-like calcium binding sequence in the heparin binding domain. With resect to Cys135, the substitutions are preferably substitutions of nucleophilic or negatively charged residues which can replace the functional role of Cys135 in catalysis. With respect to the Cardin-Weintraub-like and EF-hand-like sequences, the substitutions are preferably conservative substitutions which preserve the motif of the sequence but, as shown in the examples below, these substitutions need not be conservative in order to maintain enzymatic activity.

Thus, as a first preferred embodiment, the present invention provides a novel polysaccharide lyase comprising the mature peptide amino acid sequence of SEQ ID NO: 2 (i.e. residues 22–384) in which the residue corresponding to Cys135 has been substituted by a serine, histidine, glutamate or aspartate residue. Recombinant lyases with such a substitution have been found to have reduced initial activity ($k_{cat}$) and have particular utility when partial or slower heparin degradation is desired. Such recombinant polysaccharide lyases may optionally include the heparinase leader sequence or may include any of the other modifications described herein In another set of embodiments, the present invention provides novel polysaccharide lyases comprising the mature peptide amino acid sequence of SEQ ID NO: 2 in which one or more of the residues of the Cardin-Weintraub-like sequence, XBBXXXBXB (SEQ ID NO:3), corresponding to positions 197–205 are substituted For example, one or more of the lysine residues corresponding to positions 198, 199 or 205 of the heparin binding domain may be substituted by other positively charged residues. Such substitutions maintain the positively charged microenvironment. necessary for heparin binding and catalysis by Cys135. These substitutions may be conservative, such as replacing one or more of the two lysine residues (corresponding to positions 198 and 199 or SEQ ID NO: 2) with an arginine or histidine. Replacement of both of these residues with arginine leads to the creation of a lyase with 60% the $k_{cat}$ of native heparinase I. Alternatively, one or more of these lysines may be substituted with a small polar, small non-polar or even an acidic amino acid residue to produce a lyase with reduced activity. For example, recombinant lyases with both of these lysines replaced by alanine or aspartate have been shown to retain catalytic activity but have $k_{cat}$ values only about 4% of the native heparinase I. The lysine corresponding to position 205 of SEQ ID NO: 2, also may be modified. Substitution with an arginine or histidine is one preferred embodiment Alternatively, this residue may be substituted with a small polar, small non-polar or acidic amino acid residue. Substitution of one of these residues with a much larger residue (e.g. tyrosine), however, abolishes activity. As noted above, the histidine at position 203 of heparinase I appears to be involved in the active site as an acid/base catalyst Replacement of this residue by a neutral residue (e.g. alanine) abolishes catalytic activity. This residue may, however, be substituted, by serine, cysteine, threonine, or even the negative aspartate or glutamate to produce a polysaccharide lyase with a reduced $k_{cat}$.

The non-basic residues in the region corresponding to this first Cardin-Weintraub-like sequence may also be modified while preserving the XBBXXBXB (SEQ ID NO:3) motif by making conservative substitutions. In order to maintain heparin binding ability, the substitutions are preferably conservative with respect to residue size (e.g. Phe197→Tyr; Ile201→Leu) and charge (e.g., Ala202→Gly; Asp204→Glu). Alternatively, small polar or small non-polar residues may be substituted for any of these residues. The residue corresponding to Asn200 in SEQ ID NO: 2, for example, may be changed to a glutamine to produce a recombinant lyase. Substitution of Asn200 with alanine results in a recombinant lyase with a k of approximately 48% wild-type. The substitution of this asparagine with a lysine residue, however, is not tolerated because it is not a conservative substitution with respect to size (i.e. lysine is larger than asparagine).

In another set of embodiments, novel polysaccharide lyases are provided comprising the mature peptide amino acid sequence of SEQ ID NO: 2 win one or more residues corresponding to the EF-hand-like calcium binding domain (residues 206–220) have been substituted but calcium binding ability and catalytic activity is retained Preferably, these substitutions are conservative with respect to size and charge. Thus, one or more of the lysines corresponding to positions 208, 209, 211 or 214 may be substituted with arginine or histidine. Alternatively, one or more of these residues may be substituted with a small polar or small non-polar residue. For example, replacement of Lys214, which is not constrained in the EF-hand motif, with Ala resulted in a lyase with 60% of the $k_{cat}$ of the wild type. The aspartate residues corresponding to positions 210 and 212 of SEQ ID NO: 2 are constrained in the EF-hand sequence motif. Replacement of these residues by glutamate, however, would conform with the motif and would also constitute a conservative substitution with respect to charge and approximate size. Conservative substitutions of the neutral residues of this region may also be made as well as substitutions with small polar or small non-polar residues.

The EF-hand-like calcium binding domain has also been shown to be tolerant to some substitutions which do not conform to the EF-hand motif. Thus, for example, the substitutions of Glu207→Ala, Asp210→Ala, Asp212→Ala, and Gly213→Ala do not destroy catalytic activity but result in lyases with $k_{cat}$ values of 18%, 50%, 50%, and 20%, respectively, of the $k_{cat}$ of native heparinase I. As with the lyases with modified heparin binding domains, these recombinant lyases with reduced k have utility in that they allow for slower and more controlled degradation of heparin and other polysaccharides. In some cases double and triple mutations in the EF-hand region produce novel polysaccharide lyases having even lower enzymatic activity.

In another embodiment a novel polysaccharide lyase is provided which retains all of the enzymatic activity of the heparin I but which is not immunogenic when administered to a subject. This novel polysaccharide lyase is produced by mating a non-conservative substitution of the serine at position 39 of heparinase I which removes the glycosylation site of heparinase I. The novel substituted polysaccharide lyase is not immunogenic because the immunogenic region (glycosylation) of the lyase is removed. Preferably the serine residue corresponding to position 39 of heparinase I is substituted with an alanine residue.

In one particular embodiment, the present invention provides novel polysaccharide lyases in which the product profile is different from that of native heparinase I. In particular, polysaccharide lyases comprising the mature peptide amino acid sequence of SEQ ID NO: 2 in which the residues corresponding to Lys198 and Lys199 have been replaced by negatively charged residues (Le. Asp or Glu) produce less than 20% and, in fact, only negligible amounts of the characteristic disaccharide 1, tetrasaccharide 2 and tetrasaccharide 3 of the heparinase I product profile. Relative to heparin I, these recombinant lyases, after overnight incubation with heparin, produce about 50% of the characteristic disaccharide 2 and tetrasaccharide 1. These lyases have particular utility in the sequencing of heparin and other complex polysaccharides.

The product profile produced by the novel polysaccharide lyases includes high order low molecular weight heparin fragments which are not included in the product profile produced by native heparinase I. The high order low molecular weight fragments are large undigested fragments of heparin which have various levels of therapeutic activity attributed to larger fragments of heparin.

In another set of embodiments the invention provides novel polysaccharide lyases comprising the mature peptide amino acid sequence of SEQ ID NO: 2 in which one or more residues outside of the active site and heparin binding domain have been substituted so as to preserve the overall structure of the enzyme. In particular, polysaccharide lyases in which conservative substitutions of any of the residues of the β-strands of Table I are contemplated. Because these residues are now known not to be involved in catalysis, and because a basic model of the tertiary structure of heparinase I is now disclosed, such conservative substitutions may be made without undue experimentation and with a high expectation of success. In a particularly preferred embodiment, the residue corresponding to Cys297 may be substituted by a small polar or non-polar residue (e.g., Cys297 Ser or Cys297 Ala) without affecting enzyme activity. Although the Cys297 residue has now been shown to be irrelevant to protein activity, modification of this residue is particularly contemplated in preferred embodiments to increase stability and simplify mass production and purification by removing the possibility of unwanted disulfide cross-linking with Cys135.

The substantially pure polysaccharide lyase of the invention may also be used to remove active heparin from, a heparin contain fluid. A heparin contain fluid is contacted with the substantially pure polysaccharide lyase of the invention to degrade the heparin. The method is particularly useful for the ex vivo removal of heparin from blood. In one embodiment of the invention the substantially pure polysaccharide lyase is immobilize on a solid support as is conventional in the art. The solid support containing the immobilize polysaccharide lyase may be used in extracorporeal medical devices (e.g. hemodialyzer, pumpoxygenator) in which systemic heparinization to prevent the blood in the devise from clotting. The support membrane containing immobilized heparinase I is positioned at the end of the devise to neutralize the heparin before the blood is returned to the body.

According to another aspect of the invention, there is provided methods for treating subjects in need of depletion of circulating heparin. Effective amounts of the polysaccharides of the invention are administer to subjects in need of such treatment For example, subjects undergoing open heart surgery or hemodialysis often are in need of depletion of medically undesirable amounts of heparin in blood as a result of blood as a result of the surgery or hemodialysis. The subjects may be administered the modified heparinases of the invention in a manner and in amounts presently found acceptable when using native heparin. Effective amounts are those amounts which will result in a desired reduction in circulating heparin levels without causing any other medically unacceptable side effect Such amounts can be determined with no more than routine experimentation. It is believed that doses ranging from 1 nanogram/kilogram to 100 milligrams/kilogram, depending upon the mode of administration, will be effective. The absolute amount will depend upon a variety of factors (including whether the administration is in conjunction with other methods of treatment, the number of doses and individual patient parameters including age, physical condition, size and weight) and can be determined with routine experimentation. It is preferred generally that a maximum dose be used, that is, the highest safe dose according to sound medical judgment. The mode of administration may be any medically acceptable mode including oral, subcutaneous, intravenous, etc.

One of ordinary skill in the art, in light of the present disclosure, is now enabled to produce substantially pure preparations of any of these novel polysaccharide lyases by standard recombinant technology. That is, one may substitute appropriate codons in SEQ ID NO: 1 to produce the desired amino acid substitutions by standard site-directed mutagenesis techniques. Obviously, one may also use any sequence which differs from SEQ ID NO: 1 only due to the degeneracy of the genetic code as the staring point for site directed mutagenesis. The mutated nucleic acid sequence may then be ligated into an appropriate expression vector and expressed ill a host such as F. heparinum or E. coli. The resultant polysaccharide lyase may then be purified by techniques well known in the art, including those disclosed below and in Sasisekharan et al. (1993). As used herein, the term "substantially pure" means that the proteins are essentially f of other substances to an extent practical and appropriate for their intended use. In particular, the proteins are sufficiently pure and are sufficiently free from other biological constituents of their hosts cells so as to be useful in, for example, protein sequencing, or producing pharmaceutical preparations.

In another set of embodiments an isolated nucleic acid encoding the substantially pure polysaccharide lyase of the invention is provided. As used herein with respect to nucleic acids, the term "isolated" means: (1) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art.

As used herein, a coding sequence and regulatory sequences are said to be "operably joined" when they are covalently linked in such a way as to place the expression or transcription of the coding sequence under the influence or control of the regulatory sequences. If it is desired &hat the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribing and 5' non-translating sequences involved with initiation of transcription and translation respectively, such as a TATA box, capping sequence, CAAT sequence, and the like. Especially, such 5' non-transcribing regulatory sequences will include a promoter region which includes a promoter sequence for transcriptional control of the operably joined gene. Promoters may be constitutive or inducible. Regulatory sequences may also include enhancer sequences or upstream activator sequences, as desired As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids and phagemids. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increase in copy number within the host bacterium, or just a single time per host as the host reproduces by mitosis In the case of phage, replication may occur actively during a lytic phase or passively during a lysogenic phase. An expression vector is one into which a desired DNA sequence may be inserted by restriction and ligation such that it is operably joined to regularly sequences and may be expressed as an RNA transcript Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase or alkaline phosphatase), and genes which visibly affect the phenotype of transformed or infected cells, hosts, colonies or plaques.

Preferred vectors are those capable of autonomous replication and expression of the structural gene products present in the DNA segments to which they are operably joined.

As used herein, the term "stringent conditions" refers to parameters known to those skilled in the art One example of stringent conditions is hybridization at 65° C. in hybridization buffer (3.5×SSC, 0.02% Ficoll, 0.02% polyvinyl pyrolidone, 0.02% bovine serum albumin (BSA), 25 mM $NaH_2PO_4$ (pH7), 0.5% SDS, 2 mM EDTA). SSC is 0.15M sodium chloride/0.15M sodium citrate, pH7; SDS is sodium dodecylsulphate; and EDTA is ethylene diamine tetra acetic acid. There are other conditions, reagents, and so forth which can be used, which result in the same degree of stringency. A skilled artisan will be familiar with such conditions, and thus they are not given here. The skilled artisan also is familiar with the methodology for screening cells for expression of such molecules, which then are routinely isolated, followed by isolation of the is pertinent nucleic acid. Thus, homologs and alleles of the substantially pure polysaccharide lyases of the invention, as well as nucleic acids encoding the same, may be obtained routinely, and the invention is not intended to be limited to the specific sequences disclosed.

For prokaryotic systems, plasmid vectors that contain replication sites and control sequences derived from a species compatible with the host may be used. Examples of suitable plasmid vectors include pBR322, pUC18, pUC19 and the like; suitable phage or bacteriophage vectors include λgt10, λgt11 and the like; and suitable virus vectors include pMAM-neo, pKRC and the like. Preferably, the selected vector of the present invention has the capacity to autonomously replicate in the selected host cell. Useful prokaryotic hosts include bacteria such as *E. coli, Flavobacterium heparinum,* Bacillus, Streptomyces, Pseudomonas, Salmonella, Serratia and the like.

To express the substantially pure polysaccharide lyases of the invention in a prokaryotic cell, it is necessary to operably join the substantially pure polysaccharide lyases of the invention sequence to a functional prokaryotic promoter. Such promoters may be either constitutive or, more preferably, regulatable (i.e., inducible or derepressible). Examples of constitutive promoters include the int promoter of bacteriophage λ, the bla promoter of the β-lactamase gene sequence of pBR322, and the CAT promoter of the chloramphenicol acetyl transferase gene sequence of pPR325, and the like. Examples of inducible prokaryotic promoters include the major right and left promoters of bacteriophage λ ($P_L$ and $P_R$), the trp, recA, lacZ lacI, and gal promoters of *E. coli,* the α-amylase (Ulmanen et al., *J. Bacteriol.* 162:176–182 (1985)) and the ζ-28-specific promoters of *B. subtilis* (Gilman et al., *Gene sequence* 32:11–20 (1984)), the promoters of the bacteriophages of Bacillus (Gryczan, In: *The Molecular Biology of the Bacilli,* Academic Press, Inc., NY (1982)), and Streptomyces promoters (Ward et al., *Mol. Gen. Genet.* 203:468–478 (1986)).

Prokaryotic promoters are reviewed by Glick (*J. Ind. Microbiol.* 1:277–282 (1987)); Cenatiempo (*Biochimie* 68:505–516 (1986)); and Gottesman (*Ann. Rev. Genet.* 18:415–442 (1984)).

Proper expression in a prokaryotic cell also requires the presence of a ribosome binding site cream of the encoding sequence. Such ribosome binding sites are disclosed, for example, by Gold et al. (*Ann Rev. Microbiol.* 35:365–404 (1981)).

Because prokaryotic cells will not produce the substantially pure polysaccharide lyases of the invention with normal eukaryotic glycosylation, expression of the substantially pure polysaccharide lyases of the invention of the invention by eukaryotic hosts is possible when glycosylation is desired. Preferred eukaryotic hosts include, for example, yeast, fungi, insect cells, and mammalian cells, either in vivo or in tissue culture. Mammalian cells which may be useful as hosts include HeLa cells, cells of fibroblast origin such as VERO or CHO-K1, or cells of lymphoid origin, such as the hybridoma SP2/0-AG14 or the myeloma P3x63Sg8, and their derivatives. Preferred mammalian host cells include SP210 and J558L, as well as neuroblastoma cell lines such as IMR 332 that may provide better capacities for correct post-translational processing. Embryonic cells and mature cells of a transplantable organ also are useful according to some aspects of the invention.

In addition, plant cells are also available as hosts, and control sequences compatible with plant cells are available, such as the nopaline synthase promoter and polyadenylation signal sequences.

Another preferred host is an insect cell for example in Drosophila larvae. Using insect cells as hosts, the Drosophila alcohol dehydrogenase promoter can be used (Rubin, *Science* 240:1453–1459 (1988)). Alternatively, baculovirus vectors can be engineered to express large amounts of the substantially pure polysaccharide lyases of the invention in insects cells (Jasny, *Science* 238:1653 (1987); Miller et al., In: *Genetic Engineering* (1986), Setlow, J. K., et al., eds., Plenum, Vol. 8, pp. 277–297).

Any of a series of yeast gene sequence expression systems may also be utilized which incorporate promoter and termination elements from the genes coding for glycolytic enzymes which are produced in large quantities when the yeast are grown in media rich in glucose. Known glycolytic gene sequences can also provide very efficient transcriptional control signals. Yeast provide substantial advantages in that they can also carry out post-translational peptide modifications. A number of recombinant DNA strategies exist which utilize strong promoter sequences and high copy number plasmids which can be utilized for production of the desired proteins in yeast. Yeast recognize leader sequences on cloned mammalian gene sequence products and secret peptides bearing leader sequences (i e., pre-peptides).

A wide variety of transcriptional and translational regulatory sequences may be employed, depending upon the nature of the host. The transcriptional and translational regulatory signals may be derived from viral sources, such as adenovirus, bovine papilloma virus, simian virus, or the like, where the regulatory signals are associated with a particular gene sequence which has a high level of expression. Alternatively, promoters from mammalian expression products, such as actin, collagen, myosin, and the like, may be employed. Transcriptional initiation regulatory signals may be selected which allow for repression or activation, so that expression of the gene sequences can be modulated. Of interest are regulatory signals which are temperature-sensitive so that by varying the temperature, expression can be repressed or initiated, or which are subject to chemical (such as metabolite) regulation.

As discussed above, expression of the substantially pure polysaccharide lyases of the invention in eukaryotic hosts requires the use of eukaryotic regulatory regions. Such regions will, in general, include a promoter region sufficient to direct the initiation of RNA synthesis. Preferred eukaryotic promoters include, for example, the promoter of the mouse metallothionein I gene sequence (Hamer et al., *J. Mol. Appl. Gen.* 1:273–288 (1982)); the TK promoter of Herpes virus (McKnight, *Cell* 31:355–365 (1982)); the SV40 early promoter (Benoist et al., *Nature* (*London*) 290:304–310 (1981)); the yeast gal4 gene sequence promoter (Johnston et al., *Proc. Natl. Acad Sci.* (*USA*) 79:6971–6975 (1982); Silver et al., *Proc. Natl. Acad Sci.* (*USA*) 81:5951–5955 (1984)).

As is widely known, translation of eukaryotic mRNA is initiated at the codon which encodes the first methionine. For this reason, it is preferable to ensure that the linkage between a eukaryotic promoter and a DNA sequence which encodes the substantially pure polysaccharide lyases of the invention does not contain any intervening codons which are capable of encoding a methionine (i.e., AUG). The presence of such codons results either in a formation of a fusion protein (if the AUG codon is in the same reading frame as the substantially pure polysaccharide lyases of the invention coding sequence) or a frame-shift mutation (if the AUG codon is not in the same reading frame as the substantially pure polysaccharide lyases of the invention coding sequence).

In one embodiment, a vector is employed which is capable of integrating the desired gene sequences into the host cell chromosome. Cells which have stably integrated the introduced DNA into their chromosomes can be selected by also introducing one or more markers which allow for selection of host cells which contain the expression vector. The marker may, for example, provide for prototrophy to an auxotrophic host or may confer biocide resistance to, e.g., antibiotics, heavy metals, or the like. The selectable marker gene sequence can either be directly linked to the DNA gene sequences to be expressed, or introduced into the same cell by co-transfections Additional elements may also be needed for optimal synthesis of the substantially pure polysaccharide lyases of the invention mRNA. These elements may include splice signals, as well as transcription promoter enhancers, and termination signals. cDNA expression vectors incorporating such elements include those described by Okayama, *Molec. Cell. Biol.* 3:280 (1983).

In a preferred embodiment, the introduced sequence will be incorporated into a plasmid or viral vector capable of autonomous replication in the recipient host. Any of a wide variety of vectors may be employed for this purpose. Factors of importance in selecting a particular plasmid or viral vector include: the case with which recipient cells that contain the vector may be recognized and selected from those recipient cells which do not contain the vector, the number of copies of the vector which are desired in a particular host; and whether it is desirable to be able to "shuttle" the vector between host cells of different species. Preferred prokaryotic vectors include plasmids such as those capable of replication in *E. coli* (such as, for example, pBR322, CoIE1, pSC101, pACYC 184, and πVX. Such plasmids are, for example, disclosed by Sambrook, et al. (*Molecular Cloning: A Laboratory Manual,* second edition, edited by Sambrook, Fritsch, & Maniatis, Cold Spring Harbor Laboratory, 1989)). Bacillus plasmids include pC194, pC221, pT127, and the like. Such plasmids are disclosed by Gryczan (In: *The Molecular Biology of the Bacilli,* Academic Press, NY (1982), pp. 307–329). Suitable Streptomyces plasmids include pIJ101 (Kendall et al., *J. Bacteriol.* 169:4177–4183 (1987)), and streptomyces bacteriophages such as φC31 (Chater et al., In: *Sixth International Symposium on Actinomycetales Biology,* Akademiai Kaido, Budapest, Hungary (1986), pp. 45–54). Pseudomonas plasmids are reviewed by John et al. (*Rev. Infect. Dis* 8:693–704 (1986), and Izaki (*Jpn. J. Bacteriol.* 33:729–742 (1978)).

Preferred eukaryotic plasmids include, for example, BPV, EBV, SV40, 2-micron circle, and the like, or their derivatives. Such plasmids are well known in the art (Botstein et al., *Miami Wntr. Symp.* 19:265–274 (1982); Broach, In: *The Molecular Biology of the Yeast Saccharomyces: Life Cycle and Inheritance,* Cold Spring Harbor Laboratory, Cold Spring Harbor, N.Y., p. 445–470 (1981); Broach, *Cell* 28:203–204 (1982); Bollon et al., *J. Clin. Hematol. Oncol.* 10:39–48 (1980); Maniatis, In: *Cell Biology: A Comprehensive Treatise,* Vol. 3, Gene Sequence Expression, Academic Press, NY, pp. 563–608 (1980)). Other preferred eukaryotic vectors are viral vectors. For example, and not by way of limitation, the pox virus, herpes virus, adenovirus and various retroviruses may be employed. The viral vectors may include either DNA or RNA viruses to cause expression of the insert DNA or inset RNA. In addition, DNA or RNA encoding the substantially pure polysaccharide lyases of the invention polypeptides may be directly injected into cells or may be impelled through cell membranes after being adhered to microparticles (see below).

Once the vector or DNA sequence containing the construct(s) has been prepared for expression, the DNA construct(s) may be introduced into an appropriate host cell by any of a variety of suitable means, i.e., transformation, transfection, conjugation, protoplast fusion, electroporation, calcium phosphateprecipitation, direct microinjection, and the like. After the introduction of the vector, recipient cells are grown in a selective medium, which selects for the growth of vector-containing cells. Expression of the cloned gene sequence(s) results in the production of the substantially pure polysaccharide lyases of the invention. This can take place in the transformed cells as such, or following the induction of these cells to differentiate (for example, by administration of bromodeoxycil to neuroblastoma cells or the like).

The foregoing written specification is to be considered to be sufficient to enable one skilled in the art to practice the invention The present invention is not to be limited in scope by the particular examples disclosed herein as these embodiments are intended only as illustrations of the aspects of the invention and any recombinant polysaccharide lyases tat are functionally equivalent are within the scope of the invention Therefore, any sequences that are functionally equivalent of those described herein are within the spirit and scope of the claims appended hereto. Indeed, various modifications of the invention in addition to those shown and described herein will become apparent to those skilled in the art from the foregoing description.

EXAMPLE 1

Purification of heparinase I: Lyophilized powdered extracts of *F. heparinum* were prepared according to the method of Yang et al. (1985). Partially purified heparinase I was prepare by step gradient elution of powdered cell extracts from a hydroxyapatite column followed by reverse adsorption on a QAE-Sephadex column Further purification of the enzyme was accomplished with a chromatofocusing, 1 cm×18 cm column with PBE resin (Pharmacia). A 1.5–2.5 ml aliquot of protein (0.5–1.5 mg) in 0.01 M phosphate (pH 6.8) was applied to the column equilibrated with 0.025 M ethanolamine (pH 9.4 with acetic acid). Elution was carried out with 150 ml of 10% Polybuffer 96 (pH 6.0 with acetic acid). The chromatofocused heparinase I eluted between 10 and 15 ml (pH 8.0–8.2). Fractions (1.5–2.0 ml) were collected in tubes containing 0.2 ml of 0.5 M phosphate buffer at pH 6.8. Immediately after collection, the fractions were assayed for heparinase I activity. Prior activity determination in the presence of Polybuffer showed no inhibition or interference by the ampholytes. The active fractions were pooled, and NaCl was added from a 2.0 M aqueous solution to give a final concentration of 0.1 M. Heparinase I was concentrated and equilibrated with a buffer consisting of 0.01 M NaH$_2$PO$_4$ and 0.1 M NaCl at pH 6.8 (PBS) with Centricon P-30 microconcentrators (Amicon, Mass.). The recovery of activity from the column was up to 90%. The resulting enzyme, equilibrated with PBS, is stable for up to 5 days at 4° C.

Heparinase I was purified to homogeneity by reverse-phase high pressure liquid chromatography with an HP 1090 (equipped with a diode array detector for multiple wavelengths, an on-line chart recorder monitoring 210 and 277 nm wavelengths) on a Vydac C$_{18}$ reverse-phase column. The enzyme was eluted with a gradient of 0 to 80% acetonitrile in 0.1% TFA for 120 min. Heparinase I appeared as a doublet Both the major and minor peaks had similar UV and tryptic digest profiles (Sasisekharan, 1991). The major pa was used throughout this work. It is believed that the isoforms of heparinase I are due to some unknown post-translational modification (Zimmermann, 1989). However, the labeling results were unaffected for samples in which the two peaks were not clearly resolved (Sasisekharan, 1991). The enzyme was inactive following reverse phase BPLC. Protein concentrations were determined using Micro BCA reagent (Pierce Inc., IL) relative to a bovine serum albumin standard. To determine the purity and homogeneity of h i 1, mass spectrometry was performed on a Laser MAT (Finnigan, Calif.) (Sasisekharan et al., 1994). Amino acid composition s analysis was performed on an amino acid analyzer (Model 420, Applied Biosystems, CA) in Biopolymers Laboratory, Center for Cancer Research, MIT.

Heparinase was radio-iodinated with the Enzymobead reagent (BioRad), followed by removal of unbound [$^{125}$I] by passage over a PD10 column (Pharmacia) equilibrated with the appropriate buffer. The radio-labeled enzyme was diluted with unlabeled enzyme. The specific activity of the protein ranged 10$^4$–10$^5$ cpm/mg.

EXAMPLE 2

Pyridylethylation of cysteines: Pyridylethylation is a cysteine modification method that alkylates the cysteine using 4-vinyl pyridine (4-VP) (Andrews & Dixon, 1987). The alkylating group, 4-VP, is a hydrophobic residue that is stable in modified cysteines. The 4-VP modified cysteine(s) can be characterize easily by amino acid analysis. In this work the amino acid analyses on the 4-VP cysteine heparinase I indicated the presence of 2.14±0.2 cysteines. There was no increase in pyridylethyl cysteine content following treatment with DTT demonstrating the absence of any disulfide bonds.

EXAMPLE 3

Radio-labeling and tryptic mapping of heparinase I: Heparinase I which had been treated with 2 mM [$^3$H] iodoacetic acid in the presence of guanidine hydrochloride and DTI had ~0.55±0.05×10$^4$ cpm [$^3$H]iodoacetic acid/μg of heparinase or 2.2±0.05×10$^5$ cpm [$^3$H]iodoacetic acid/nmole of heparinase. Physical mapping of the cysteines of heparinase I was performed by peptide mapping with trypsin, followed by amino acid sequencing. The [$^3$H]labeled peptides were peak 7 or Cys135, peak 65 or Cys297, and a third peak: peptide 61 which also turned out to be Cys297. The sequences of the three peptides corresponding to these peaks were:

Peak7 KGIC*EQGSSR
Peak65 KMPFAQFPKDIC*WITFDVAIDWTK
Peak61 KDIC*WITFDVAIDWTK

The above results show that mature heparinase I from *F. heparinum* contains two free cysteines and not a disulfide bridge.

EXAMPLE 4

Modification with Organomercurials: The reversible, sulfhydryl specific anion, PCMB, was utilized to determine the effects of sulfhydryl modification on heparinase I activity. Chromatofocused heparinase I treated with PCMB at 2.5–100 μM and 4° C. resulted in a reversible loss of 95±5% of enzyme activity. Upon addition of 10 mM DTF, up to 90% of the lost enzyme activity is recovered within 1 h at 4° C., verifying the sulfhydryl specificity of the reaction. Overnight incubations did not result in further inactivation of the enzyme, and 90% of the activity was recovered subsequently by treatment with 10 mM DTI. The time course of inactivation in the presence and absence of heparin also was determined. In the presence of 0.5 mg/ml heparin (~5×K$_m$), the rate of inactivation was significantly decreased Rate constants were determined by assuming pseudo first order kinetics and fitting of the data to the equation:

$$A_t = A_o \exp(-t/\tau) + A_\infty$$

where $A_t$ is the fractional activity at time t, $A_o$ is the initial factional activity, $A_\infty$ is the residual activity at infinite time, and τ is the inactivation time constant in minutes or the reciprocal rate constant. Time constants were obtained by a nonlinear least squares fit of the data to the equation. The best fit parameters obtained in the absence of heparin were $A_o$=0.72±0.05, $A_\infty$= 0.25±0.03, and τ=0.8±1 min. In the presence of 0.5 mg/ml heparin, the best fit parameters were $A_o$=0.67±0.08, $A_\infty$=0.28±0.03, and τ=5±1 min. The corresponding rate constants with 0.0 and 0.5 mg/ml heparin are 1.2 min$^{-1}$ and 0.2 min$^{-1}$, respectively. Thus the presence of heparin reduces the inactivation rate 6&fold. The heparin concentration in the assay medium (25 mg/ml) was much larger than the K$_m$ of 0.1 mg/ml (Yang et al., 1985); consequently, any additional heparin introduced did not alter the kinetics.

The use of PCMB-sulfonic acid resulted in similar inactivation behavior. PCMBS treatment was carried out following reduction with DTT in order to ascertain whether the modifications of any exposed sulfhydryls affected the activity. Heparinase I pretreated with 1 mM DTT for 4 h at 4° C. under nitrogen followed by modification with 2.5 mM PCMBS resulted in the same reaction kinetics as observed with untreated heparinase. Heparin was not included in these experiments. Further, similar heparinase inactivation results were obtained when recombinant heparinase I was used in the PCMB labeling studies.

EXAMPLE 5

N-ethylmaleimide Derivatization: Different sulfhydryl reagents often exhibit disparate reactivities with proteins due to protein structural properties (Vallee & Riordan, 1969). The effect of NEM modification on heparinase I activity was examined in an attempt to elucidate structural influences on the cysteine reactivities. Treatment of heparinase I with 1 mM NEM at pH 7.0, showed little change in activity over an 8 h period He I ted with 1 mM NEM overnight at 4° C., result in an activity loss of about 15%. In contrast, in the presence of 10 mM NEM pH 7.0 at 4° C., 15% of the enzymatic activity was lost within 45 min.

In order to ascertain whether significant levels of NEM bind heparinase I, labeling studies with [$^3$H]NEM were undertaken. Non-denatured heparinase incubated with 1 mM [$^3$H]NM for 8 h incorporates $0.3 \times 10^{-9}$ nmole [$^3$H]NEM/μg heparinase I, as determined from radio-labeled heparinase I electroeluted from an SDS gel. If the reaction was allowed to proceed for 20 h, up to $1 \times 10^{-9}$ nmole [$^3$H]NEM/μg heparinase I was incorporated with a corresponding 15% loss of activity. In contrast, if the enzyme was first denatured by incubation with either 0.1% SDS or 5 M guanidine hydrochloride, about $6 \times 10^{-9}$ mmole [$^3$H]NEM/μg heparinase I was incorporated within an 8 h incubation at 4° C.

EXAMPLE 6

Derivatization by Iodoacetamide and Iodoacetic Acid: The effect of reagent charge on cysteine reactivity was investigated by use of the negatively charged reagent iodoacetic acid and its neutral analogue, iodoacetamide. In addition to their charge difference, the reactivity of iodoacetamide is 5–7 times faster than iodoacetic acid with free cysteine in aqueous media (MacQuarrie & Bernhard, 1971).

Heparinase I incubated with 2, 5, 10, and 120 mM iodoacetanide in PBS at pH 7.0 and 4° C. for up to 24 h exhibited little change in activity. A 15% inactivation occurred only after a 24 h incubation in the presence of 120 mM iodoacetamide. Iodoacetamide, therefore, does not significantly modify heparinase I.

In contrast, in the presence of 2 mM iodoacetic acid in PBS at 4° C., 95±5% of heparinase I was inactivated within 10 min. The inactivation rate was concentration dependent: at 1 mM and 0.1 mM iodoacetic acid, inactivation was complete within 15 min and 15 h, respectively. The sensitivity of the iodoacetic acid binding site to the presence of heparin was demonstrated by the decrease in the inactivation rate in 500 mM iodoacetic acid from $3 \pm 1 \times 10^{-3}$ h$^{-1}$ to $5 \pm 2 \times 10^{-4}$ h$^{-1}$ the presence of 2 mg/ml heparin. The retention of activity relative to untreated heparin I was 15±5%. Pretreatment of the enzyme for 4 h at 4° C. with DTT under nitrogen had no effect on the modification.

It is known that the iodoacetic acid reactive form of cysteine is the mercaptide anion, and that the reaction rate increases with increasing pH (Torchinsky, 1981). In particular, the relative fee cysteine alkylation rates at pH 5.6, pH 7.02, and pH 8.36 are 0.14, 1.0, and 2.1, respectively (Torchinsky, 1981). If the heparinase I cysteine were unaffected by the presence of nearby amino acids in the protein, the iodoacetic acid inactivation rates at 6.5 and 8.0 would be expected to vary by an order of magnitude. The pseudo first order heparinase I inactivation rate constants obtained at pH 6.5, 7.0, 7.5, 8.0 and 8.5, however, varied very little over the pH range. The rate constants, k, were determined from the activity after a determined time, A, the initial activity $A_o$, the residual activity at infinite time, $A_\infty$, and the equation:

$$k = (1/\tau) ln[(A_t - A_{28})/A_0]$$

The small variation in the rate of inactivation suggests that the cysteine was activated by the presence of nearby basic amino acids (Hammond & Gutfreund, 1959, Rabin & Watts, 1960).

The above results, i.e the marginal modification of heparinase I by iodoaceide and the significant inactivation of heparinase I by iodoacetic acid, corroborates with the hypothesis that the environment around the cysteine residue is basic.

EXAMPLE 7

Salt of PCMB labeling: In order to show that the positive environment around the PCMB reactive cysteine influences the labeling of the negatively charged PCMB, cysteine labeling by PCMB was performed under different salt concentrations and the tine course of inactivation of heparinase I by PCMB with increasing salt concentrations was calculated. Heparinase I inactivation rate by PCMB was significantly reduced with increasing salt concentration 50, 100 and 200 mM NaCl. Indeed, no inactivation was detectable at a salt concentration of 200 mM NaCl. This result is consistent with the observation that the environment around the cysteine is positively charged, and the alteration of the electrostatic properties of this region by changing the salt concentration has a significant effect on the rate of the PCMB based inactivation of the thiol group. Thus, this result supports the conclusion that the environment around the PCMB-reactive cysteine is basic.

EXAMPLE 8

Mapping the Modified Cysteine: In order to further verify that the PCMB-reactive cysteine was at the same site as the iodoacetic acid binding cysteine, [$^3$H]iodoacetic acid was reacted with nondenatured PCMB-modified heparinase 1, and the amount of label incorporated was compared to that of nondenatured, untreated heparinase I labeled with [$^3$H] iodoacetic acid under identical conditions. In these experiments, it was found that the [$^3$H]iodoacetic acid labeling was reduced by 80% following treatment with PCMB. This suggested that the iodoacetic acid binding site and the PCMB binding site are identical. This was conclusively determined by peptide mapping by trypsin digestion and amino acid sequencing of the modified heparinase I cysteine.

The PCMB-labeled heparinase I was isolated, denatured and then reacted with iodoaceamide to block the other cysteine. Following this, the enzyme was treated with DTT to remove the bound PCMB, and then labeled with [$^3$H] iodoacetic acid. Modified heparinase I was digested with trypsin and the tryptic peptides were separated. Only one cysteine, Cys135, was selectively labeled by [$^3$H]iodoacetic acid. Cys297 was not labeled by [$^3$H]iodoacetic acid in this experiment In another experiment, heparinase I was first labeled at the reactive cysteine with PCMB. The enzyme was then denatured, labeled with [$^3$H]iodoacetic acid, and are chromatographed to remove the excess radiolabel. Following this, the enzyme was digested with trypsin and the tryptic peptides were shed by RP-HPLC. In this experiment Cys297 was selectively [$^3$H]labeled, while Cys135 was not. The results of the above experiments taken together, confirm that Cys135 is the PCMB-labeled or the active site cysteine. In addition, [$^3$H]iodoacetic acid labeling had little or no cross-reactivity and was selective in labeling the cysteines.

EXAMPLE 9

Cysteine-Modified Recombinant Heparinase: Site-directed mutations were performed to confirm the role of Cys135 in heparinase I activity. Seven mutant recombinant heparinases were designed: C135S (Cys135 to serine conversion), C135H (Cys135 to histidine conversion), C135E (Cys135 to glutamate conversion), C135D (Cys135 to aspartate conversion), C135A (Cys135 to alanine conversion), C297S (Cys297 to serine conversion), and C297A (Cys297 to alanine conversion).

Recombinant polysaccharide lyases were produced as soluble protein in BL21DE3 *E. coli* host, using the pET 15b system, where expression is driven by bacteriophage T7 Polymerase. This construct has a histidine tag (6 consecutive histidines), which constitutes a high affinity site for Ni$^{2+}$, and a thrombin cleavage site in a 21 amino acid N-terminal leader sequence. The expression is induced by IPTG (isopropyl-β-D-thiogalactoside). The -L heparinase construct starts with a sequence which reads Met, Gln22, Gln23, Lys24, Lys25, Ser26 ... (Sasisekharan et al., 1993). The Met residue was added before the Gln22 to introduce a start codon. The Cys135 and Cys297 mutations were introduced as part of PCR primers. These primers, together with the T7 promotor (5') and T7 terminator (3') primers (Novogen, Wis.) (which flank the heparin gene), were used to create two PCR products that overlap in sequence, with the -L heparinase gene construct as a template. The overlapping products were isolated from low melt agarose (Seaplaque, FMC, or GIBCO BRL, Gaithersburg, Md.), denatured (100° C.), and allowed to reanneal (room temperature) to produce two possible heteroduplex products (Higuchi, 1990). The heteroduplex with the recessed 3' ends was filled-in using Taq polymerase. This fragment was used as a template in a 12 cycle PCR (Higuchi, 1990) with the 5' and the 3' primers respectively. The PCR product was isolated from a low melt gel and ligated overnight directly into T-vectors (Marchuk, et al., 1991). T-vector was prepared as described in Marchuk et al., 1991. Briefly, pBluescript (Stagene, LaJolla, Calif.) was digested with EcoRV (New England Biolabs, Beverly, Mass.) and isolated and gel purified from a low melt gel. The purified linear plasmid was then incubated with Taq polymerase (1 unit/μg plasmid/20 μl volume) (Perkin Elmer, Norwalk, Conn.) and 2 mM dTTP for 2 hrs at 70° C., using standard buffer conditions. The sub-cloned heparinase I PCR fragments were excised from T-vector by digestion with NdeI and BamHI, gel purified, and then ligated into pET-15b plasmid predigested at the NdeI and BamHI sites and gel purified) using T4 DNA ligase (New England Biolabs, MA). The ligation mixture then was used to transform DH5α competent cells (GIBCO BRL). The plasmid containing the recombinant lyase gene in pET-15b was isolated purified using Miniprep (Qiagen, Charsworth, Calif.), and used to transform the host cell BL21(DE3) (Novogen, Wis.). Recombinant heparinase I construct devoid of the putative signal sequence (-L r-heparinase I) was also expressed as a control (Sasisekharan et al., 1993).

The constructs were transformed in BL21DE3) (Novagen), grown overnight, diluted in 100 ml LB, 250 μg/ml ampicillin and grown to an $OD_{600}$ of 0.5. The culture was induced with 1 mM IPTG for 2 hours, harvested by centrifugation (4° C., 3500g×10 min), washed in cold phosphate buffered saline (PBS) and resuspended in ½0th volume binding buffer (20 mM Tris, 500 mM NaCl, 5 mM Imidazole). The resuspended culture was placed in an ice bath, sonicated for 2 min using a Branson 450 sonicator (Branson, Danbury, Conn.) (power 3, 50% pulse) and centrifuged at 4° C. and 15,000 g for 30 min. The supernatant was assayed for activity and purified by $Ni^{2+}$ affinity chromatography using sepharose 6B Fast Flow resin covalently linked to nitrilotriacetic acid (Novogen, Wis.). Briefly, the resin was charged with 5 column volumes 200 mM $NiSO_4$ and equilibrated with 5 column volumes binding buffer. Then, 6–10 ml sample was applied followed by 12 ml binding buffer, 9 ml 15% elution buffer (20 mM Tris, 500 mM NaCl, 200 mM Imidazole) and 10 ml 100% elution buffer. The enzymes were recovered in 4 ml of the 100% elution step, desalted on two PD10 columns (BioRad, Richmond, Calif.) and incubated overnight at 4° C. with 0.5 units thrombin (Novagen, Wis.). Cleaved enzymes were applied to the stripped (20 mM Tris, 500 mM NaCl, 100 mM EDTA) and regenerated column and collected in the flow through fraction. SDS-PAGE (Laemmli, 1970) was carried out using precast 12% gels and a Mini Protean II apparatus, and stained with the Silver Stain Plus kit.

The level of protein expression for all the recombinant heparinases was identical in the BL21(DE3) host While -L r-heparinase I control was expressed as a soluble protein in *E. coli* with an activity of ~5.2 U/mg of *E. coli* crude extract (Sasisekharan et al., 1993), the C135A r-heparinase I was express in BL21(DE3) with no enzymatic activity. Interestingly, the C135S r-heparinase I was expressed in BL21(DE3) with an activity of ~0.06 U/mg of *E. coli* crude extract The C135H, C135E, and C135D recombinants show ~50% of the activity of the -L r-heparinase. Importantly, the mutations at Cys297 (C297S and C297A) were both expressed in the same host with no change in their enzymatic activity compared to the -L r-heparinase I control.

The r-heparinase degradation of heparin was identical to that of the purified *F. heparinum* heparinase 1, producing the two di-, the three tetra-, and the hexasaccharides. The above results taken together show that Cys135 is important for heparinase I activity and that altering Cys297 did not alter heparinase I activity.

EXAMPLE 10

Calcium Dependence of Heparinase I Activity: Heparinase I samples were extensively desalted using Centricon P-30 microconcentrator to remove residual calcium from the hydroxylapatite step during the enzyme purification (Yang, et al., 1985; Sasisekharan et al., 1994). The heparin concentration was fixed at 25 mg/ml in all experiments, and only the calcium concentration was varied. Activity was seen to increase with calcium concentrations increasing up to about 5–10 mM. A region of heparinase I (residues 206–213) was found to be homologous to the calcium binding loop of the EF-hand structural domain (Kretsinger et al., 1991). Of the five amino acids that are involved in coordinating calcium, four are conserved in heparinase I (Table II). Also the glycine and hydrophobic residue at the top of the loop are conserved This suggested a calcium coordinating site in heparinase I.

EXAMPLE 11

Heparin Affinity Chromotography: The affinity separation of heparinase I was carried out in the presence and absence of calcium Heparinase I was seen to bind to heparin-POROS, and the bound enzyme could be eluted at a salt concentration of about 200 mM. The protein eluted a; a doublet, consistent with results from heparinase I purification (Sasisekharan, et al., 1993). When the affinity separation was carried out in the presence of calcium (5mM), heparinase I eluted in the void volume since the enzyme cleaves the heparin to which it binds (this was confirmed by the appearance of oligosaccharide products in the void volume).

EXAMPLE 12

Affinity Co-electrophoresis: Affinity co-electrophoresis (ACE) was used to quantify heparin binding to heparinase I. The technique measures the extent of binding based on the retardation of heparin when electrophoresed in the presence of heparinase I embedded in an agarose gel. ACE was carried out in the presence or absence of iodoacetic acid to determine the importance of the active site Cys135 in the binding of heparin to heparinase I and in the absence lo of calcium to prevent heparin degradation. At a sufficiently high enzyme concentration, the migration of heparin is retarded in a dose-dependent manner. There is no difference in the retardation of heparin for the iodoacetic acid modified heparinase I when compared to the unmodified heparinase I. This result indicates that blocking the active site cysteine does not alter heparin binding.

To determine a binding constant, a Scatchard plot was obtained by plotting R/C vs. R, where R is the retardation coefficient $R=(M_--M)/M_0$, $M_0$ is the mobility of free heparin, and M is the observed heparin mobility in a zone with protein concentration of C. Assuming a single site, bimolecular association, the data were fitted to a straight line with a slope of $-1/K_d$ (Lee and Lander, 1991). The dissociation constant for heparinase-heparin binding was found to be 60 nM by this technique. Furthermore, an ACE gel of heparin-heparinase carried out in the presence of calcium showed extensive smearing of the heparin band, since heparinase I cleaved heparin in the presence of calcium. No heparin retardation could be observed on this gel.

EXAMPLE 13

Heparin Blotting of CnBr Digests of Heparinase I: CnBr digested here I separated by SDS-PAGE resulted in 10 peptide fragments. Heparinase I contains 5 internal methionine residues (CnBr sites) two of which are adjacent, so for complete digestion, only 5 fragments should be expected. Only 4 of the smaller peptides could be sequenced as the larger fragments, based on molecular weights and sequencing, probably represented partial digests from the N-terminus which previously was shown to be blocked (Sasisekharan, et al., 1993). The CnBr digested heparinase I fragments were transferred onto nitrocellulose and hybridized with labeled heparin, and counted for $^{125}$I incorporation. The binding of $^{125}$I-heparin to one peptide band (CnBr-8), was 2–4 times as high as binding to the other bands and to controls. Similar results were obtained by an alternative method where the peptide bands were cut out and then hybridized individually. CnBr-8 is a partial digest of approximately 10 kDa, spanning amino acids 196 to approximately 290 of the heparinase I primary sequence. It has a lysine rich N-terminal region, containing two Cardin-Weintaub En binding consensus sequence and a calcium binding loop of the EF-hand structural domain. CnBr-7 is ~13-kDa, spanning amino acids 272 to approximately 360. The legion from 272 to 290 is common to CnBr-7 and CnBr-8 and, since CnBr-7 did not bind heparin, it is thus excluded from being a part of the heparin binding domain. These results indicates the region 195–270 contains the primary heparin binding site and that this site is still functional in the isolated CnBr-8 peptide. To further narrow down the heparin-binding region, we performed tryptic digests which cleave heparinase I to much smaller fragments than CnBr.

EXAMPLE 14

Competitive Binding and Dot-blots with Tryptic Digests of Heparinase I: Tryptic mapping of heparinase I has been standardized using RP-HPLC (Sasisekharan, et al., 1993). Even though heparinase I is a very basic protein (having a pI of 9.1), it binds very well to a hydrophobic surface as its elutes at a relatively high acetonitrile concentration of 72% in RP-HPLC. Interestingly, we found that heparin, but not chondroitin sulfate, was able to prevent heparinase I binding to a reverse-phase column in a concentration dependent manner.

We tested the ability of heparin in protecting the heparin binding domain of heparinase I from trypsin cleavage. Under the conditions tested, we observed that heparin was ineffective in protecting the heparin binding domain but, nonetheless, it was able to specifically compete with the binding of some heparinase I tryptic peptides to the reverse phase column. Peaks that shifted significantly in their elution time, or disappeared (presumably eluting in the void volume), represent tryptic peptides that binds to heparin Chondroitin sulfate was used as a control to account for non-specific ionic effects of heparin on elution of the peptides. Compared to a control tryptic map, no significant changes were observed in the tryptic digests performed in the presence of increasing concentration of chondroitin sulfate except for the appearance of a peak about 42 min and the overall diminishing of peak sizes for td9, those eluting between 52–58 mins, and td50. However, in the presence of increasing concentrations of heparin, the following peaks were altered reproducibly: td4, td9, peaks eluting between 52–58 mins td39, td 45, td 50. As peptides td9, those eluting in the region between 52-58 mins, and td5o were altered by both heparin and chondroitin sulfate, it is probable that these peptides non-specifically interact with these acidic polysaccharides. However, in the presence of heparin alone (or heparin with chondroitin sulfate) td4, td39 and td45 were absent (from the region where they should elute) in the tryptic map, indicating specific binding to heparin In a dot blot assay, for specific binding of $^{125}$I heparin to heparinase I tryptic peptides, in the presence of a 100 fold excess of cold a chondroitin sulfate, only td45 showed $^{125}$I signal. In addition, there were $^{125}$I signals near the isocratic region of the chromatogram where di- and tri-peptides, containing Lys and Arg residues, elute.

The sequences of tryptic peptides from heparinase I are given in Table III. It can be concluded it td45 (residues 215–221) and td4 (residues 132–141) are the only peptides from the tryptic digest experiments that bind specifically to heparin; consistent with td39 being a part of CnBr-8 peptide, and td4 being a part of the active site of heparinase I. The combined heparin binding results from experiments with CnBr and tryptic digests of heparinase I points to the region of residues 195–221 as being directly involved in heparin binding. Importantly, the region from 195–220 contain multiple lysines and is likely to be degraded to very short peptides (di and tripeptides) by trypsin. Thus, it would not have been expected to show up on the tryptic digest chromatogram.

EXAMPLE 15

Synthetic Heparin Binding Domain of Heparinase I: The region 196–213 was synthesized as a peptide (HBP-I). The peptide (HBP-I) has a 4 micromolar binding affinity for heparin dodecasaccharides. Interestingly, HBP-I affected the product profile of heparinase I degradation of heparin. As mentioned earlier, heparinase depolymerization of heparin results in two disaccharides, three tetrasaccharides (1–3), and a hexasaccharide. In a concentration dependent manner, the addition of HBP-I to the reaction mixture caused the peak corresponding to tetrasaccharide 3 ($\Delta U_{2S}H_{NS,6S}I_{2S}H_{NS,6S}$) to disappear. When tetrasaccharide 3 was isolated and degraded with heparin I in the presence of HBP-I, a marked increase in the amount of disaccharide was observe A control pride with similar charge properties (and at the concentration ranges tested above) had no effect on the enzyme activity or on the oligosaccharide product profile. This demonstrates that HBP-I affects the selectivity of heparin degradation by heparinase I: Tetrasaccharide 3, but not tetrasaccharides 1 or 2, is degraded to a large extent in the presence of HBP-I.

EXAMPLE 16

PCMB Protection and Tryptic Digest: Heparinase I derivitization by sulfhydryl specific reagent PCMB inactivated the enzyme due to selective modification of the active site cysteine or Cys135 (see above). Further, the inability to selectively label Cys135 using PCMB in the presence of heparin indicated the existence of a heparin binding site in close proximity to Cys135. To test this hypothesis, tryptic digestion of PCMB modified heparinase I (PCMB-heparinase I) was carried out to determine if PCMB was able to protect the heparin binding sequence from trypsin cleavage. The PCMB-heparinase I tryptic map was marked by the appearance of a new peak. The peptide corresponding to this new peak consisted of residues 200–209 of heparinase I. This result suggests that PCMB labeled Cys135 protects this lysine-rich peptide (the heparin binding sequence) from trypsin cleavage, when compared to a control digest where this peptide is not observed This result is consistent with the notion of a heparin binding site in close proximity to the active site Cys135.

EXAMPLE 17

Binding Domain-Modified Recombinant Heparinase: To further investigate the function of the heparin/calcium binding domain, a series of recombinant lyases were produced in which the binding domain was modified by site-directed mutagenesis. The recombinants were produced by the same method described above for cysteine mutants.

For example, a mutant with His203 to alanine conversion (H203A) was constructed and both the mutant and the wild type r-heparinase I were expressed in *E. coli.* -L r-heparinase I degradation of heparin was identical to that of the purified *F. heparinum* heparinase I, producing the two di-, the three terra-, and the hexasaccharides described above. The H203A mutant, on the other hand was completely inactive. Estimated from the intensity of the purified bands, the combined yield of protein expression and purification is identical for both wild type and mutant heparinase. This result demonstrates that His203 is critically required for enzyme activity. In addition, the results strongly suggests that the heparin binding region around residue 203 is in close proximity to the scissile bond during catalysis.

As additional examples, recombinant polysaccharide lyases were produced by site-directed mutagenesis in which Lys198 and Lys199 were substituted by alanine (K198A, K199A), aspartate (K198D, K199D) and arginine (K198R, K199R). The replacement of the positively charged lysine with the positively charged arginine had no apparent effect on activity or product profile. Replacement of either lysine with the neutral alanine or negative aspartate resulted in product profiles in which disaccharide 1 and tetrasaccharides 2 and 3 were negligible and disaccharide 1 and tetrasaccharide 2 were reduced to approximately 50% of the abundance obtained with native heparinase I.

Other recombinant polysaccharides produced in accordance with the present invention are shown in Table IV along with indications of their $k_{cat}$ values and activity after overnight incubation with heparin. These polysaccharide lyases are illustrative and not exhaustive of those enabled by the present disclosure.

TABLE I

| Turn # | PB1 | PB2 | PB3 |
|---|---|---|---|
| 1 | 26–30 | 35–38 | |
| | SGNIP | VQAD | |
| 2 | 48–51 | 53–56 | |
| | NKWV | VGIN | |
| 3 | 67–70 | 75–77 | |
| | LRFN | YRF | |
| 4 | 107–110 | 116–117 | 120–122 |
| | TNDF | SV | NAQ |
| 5 | 128–131 | 140–143 | 146–148 |
| | YHYG | SRSY | SVY |
| 6 | 154–156 | 159–160 | 164–167 |
| | PDN | TI | WHGA |
| 7 | 171–175 | 178–179 | 181–184 |
| | TLVAT | GE | KTLS |
| 8 | 215–218 | 225–227 | |
| | ITYV | WKV | |
| 9 | 234–238 | | 243–247 |
| | TLAFG | | YFYIK |
| 10 | 261–264 | 265–267 | |
| | RNNA | NPE | |
| 11 | 297–299 | 301–304 | |
| | CWI | FDVA | |
| 12 | 323–329 | | 338–341 |
| | DVMMTY | | AHIV |

TABLE II

| EF-hand homology | n | c | x | x | c | x | c | gly | x | h | c | x | x | c | n |
|---|---|---|---|---|---|---|---|---|---|---|---|---|---|---|---|
| Heparinase I | $V_{206}$ | E | K | K | D | K | D | G | K | I | T | Y | V | A | $G_{220}$ |
| Score | + | + | | | + | | + | + | | + | + | | | – | – |

The table shows the central $Ca^{2+}$ coordinating homology domain of EF-hands, with the functional amino acids bolded (Kretsinger, 1975).

"c" indicates the $Ca^{2+}$ coordinating amino acids, DN, STE or Q.

"h" indicates amino acids with hydrophobic side groups, I, L or V.

"n" indicates nonpolar amino acids, I, L, V, M, F, Y, W.

"X" indicates any amino acid.

TABLE III

| Peptides | Amino Acid Sequence |
|---|---|
| td 4 | (K,R) G I C E Q G S S R |
| td 9 | (K,R) T V Y H Y G K |
| td 9' | (K,R) T S T I A Y K |
| td 21 | (K,R) F G I Y R |
| td 33 | (K,R) A D I V N Q Q E I L I G R D D* G Y Y F K |
| td 39 | (K,R) I T Y V A G K P N G N K V E Q G G Y P T L A F* |
| td 43 | (K,R) M P F A Q F P K D C W I T F D V A I D* T K |
| td 40 | (K,R) N L S G Y S E T A R |
| td 45 | K N I A H D K V E K K |

TABLE III-continued

| Peptides | Amino Acid Sequence |
|---|---|
| td 72 | K T L S I E E F L A L Y D R |
| td 50 | R S Y T F S V Y I P S S F P D N A T T I F A Q W H G A P S R T L V A T P E G E I K |

The table shows the peptides from tryptic digest of heparinase I. The sequence begins (K,R) because trypsin cuts at either lysine or arginine residues. * represents amino acids that could not be determined.

TABLE IV

| MUTANT | $K_{cat}$ (s$^{-1}$) | Products (% wild type) |
|---|---|---|
| C135A | 0 | none |
| C135D | 3.5 | ~50 |
| C135E | 3.8 | ~50 |
| C135S | 2 | <10 |
| C135H | 3 | ~50 |
| H203A | 0 | none |
| H203D | 3.5 | ~10 |
| H203S | 3.2 | ~10 |
| H203C | 3.9 | ~10 |
| KK198AA | 4.1 | ~50 |
| KK198DD | 4.1 | ~50 |
| KK198RR | 54 | equivalent |
| KK208AA | 24 | ~70 |
| KK208DD | 54 | equivalent |
| KK208RR | 60 | equivalent |
| N200A | 48 | equivalent |
| N200K | ~0 | none |
| K205A | 22 | equivalent |
| K205Y | ~0 | none |
| E207A | 18 | ~70 |
| D210A | 50 | equivalent |
| D212A | 50 | equivalent |
| G213A | 20 | ~25 |
| K214A | 60 | equivalent |
| Recomb hep | 92 | equivalent |
| Native hep | 100 | |

REFERENCES

Andrews, P. C., & Dixon, J. E. (1987) Anal. Biochem. 161:524–528.

Bernstein, H., Yang, V. C., Cooney, C. L., & Langer, R. (1988) Methods in Enzymol. 137:515–529.

Cardin, A. D., & Weintraub, H. J. R. (1989) Arteriosclerosis 9:21–32

Comfort, A. R, Albert, E., & Langer, R. (1989) Biotech. and Bioeng. 34:1383–1390.

Hammond, B. Y., & Gutfreund, H. (1959) Biochem. J. 72:349–353

Hardingham, T. E., & Fosang, A. J. (1992) FASEB J. 6:861–870

Higuchi, R. (1990) PCR Protocols: A Guide to Methods and Applications (Innis, M. A., Gelfand, D. H., Sninsky, J. J., & White, T. J., eds) pp. 177–183, Academic Press Inc., NY Jackson, R. L., Busch, S. J., & Cardin, A. D. (1991) Physiol. Rev. 71:481–539.

Kjellen, L., & Lindahl, U. (1991) Annu. Rev. Biochem. 60:443–475.

Kretsinger, R. H. (1975) in Calcium Transport in Contaction and Secretion, Carafoli et al. (eds.), North-Holland Publishing Co., Amsterdam, pp 469–478.

Kretsinger, R. H. (1980) CRC Crit Rev. Biochem. 8:119–174.

Laemmli, U. K. (1970) Nature 227:680–685.

Leckband, D., & Langer, R. (1991) Biotech. Bioeng. 37:227–237.

Lee, M. K., & Lander, A. D. (1991) Proc. Natl. Acad. Sci. (USA) 88:2768–2772

Linhardt, R. J., Fitzgerald, G. L., Cooney, C. L., & Lahger, R. (1982) Biochem. Biophys. Acta 702:197–203.

Linhardt, R. J., Galliher, P. M., & Cooney, C. L. (1986) Appl. Biochem. Biotechnol. 12:135–176.

Linhardt, R. J., Turnbull, J. E., Wang, H. M., Longanathan, D., & Gallagher, J. T. (1990) Biochemistry 29:2611–2617.

Linker, A., & Hoving, P. (1972) Methods in Enzymol. 28:902–911.

Lohse, D. L., & Linhardt, R. J. (1992) J. Biol. Chem. 267:24347–24355.

MacQuarrie, R. A., & Berhard, S. A. (1971) Biochemistry 10:2456–2460

Rabin, B. R., & Watts, D. C. (1960) Nature 188:1163–1165

Sasisekharan, R. (1991) Ph.D. Thesis, Harvard University, Cambridge, Mass.

Sasisekharan, R,. Bulmer, M., Moremen, K., Cooney, C. L., & Langer, R. (1993) Proc. Natl. Acad. Sci. (USA) 90:3660–3664.

Sasisekharan, R, Moses, M. A., Nugent, M. A., Cooney, C. L., & Langer, R. (1994) Proc. Nat. Acad. Sci. (USA) 91:1524–1528.

Torchinsky, Yu. M.(1981) Sulfur in Proteins Pergamon Press Inc., N.Y.

Vallee, B., & Riordan, J. F. (1969) Ann. Rev. Biochem. 38:733–794.

Yang, V. C., Linhardt, R. J., Bernstein, H., Cooney, C. L., & Langer, R. (1985) J. Biol. Chem. 260:1849–1857.

We claim:

1. An enzymatically active substantially pure polysaccharide lyase comprising the amino acid sequence of the mature peptide of SEQ ID NO: 2 wherein at least one amino acid residue has been substituted and wherein
the substitution is selected from the group consisting of (a) a substitution of a cysteine residue corresponding to position 135 of SEQ ID NO: 2 with a residue selected from the group consisting of aspartate, glutamate, serine, threonine, and histidine; (b) a conservative substitution of a residue of a Cardin-Weintraub-like heparin-binding sequence XBBXXXBXB (SEQ ID NO:3) corresponding to positions 197–205 or 208–212 of SEQ ID NO: 2, wherein the conservative substitution includes the replacement of a basic residue, B, with a basic amino acid or replacement of a non-basic residue, X, with an amino acid which is a conservative substitution; (c) a conservative substitution of a residue of an EF-hand-like calcium binding sequence of SEQ ID NO: 9 corresponding to positions 206–220 of SEQ ID NO: 2; (d) a conservative substitution of a residue of a turn of a PB1, PB2 or PB3 β-sheet domain of SEQ ID NO: 2, the turns of PB1 β-sheet domain corresponding to positions 26–30, 48–51, 67–70, 107–110, 128–131, 154–156, 171–175, 215–218, 234–238, 261–264, 297–299, or 323–329 of SEQ ID NO: 2, the turns of PB2 β-sheet domain corresponding to positions 35–38, 53–56, 75–77, 116–117, 140–143, 159–160, 178–179, 225–227, 265–267, or 301–304 of SEQ ID NO: 2, and the turns of PB3 β-sheet domain corresponding to positions 120–122, 146–148, 164–167, 181–184, 243–247, or 338–341 of SEQ ID NO: 2; (e) a non-conservative substitution of a cysteine residue corresponding to position 297 of SEQ ID NO: 2; (f) a non-conservative substitution of a residue of a turn of a PB1, PB2 or PB3 β-sheet domain of SEQ ID NO: 2 wherein the turns of PB1 β-sheet domain corresponding to positions 26–30, 48–51, 67–70, 107–110, 128–131, 154–156, 171–175, 215–218, 261–264, 297–299, or 323–329 of SEQ ID NO: 2, the turns of PB2 β-sheet domain corresponding to positions 35–38, 53–56, 75–77, 116–117, 140–143, 159–160, 178–179, 225–227, 265–267, or 301–304 of SEQ ID NO: 2, and the turns of PB3 β-sheet domain corresponding to positions 120–122, 146–148, 164–167, 181–184, 243–247, or 338–341 of SEQ ID NO: 2; (g) a substitution of a histidine residue corresponding to position 203 of SEQ ID NO: 2 with a residue selected from the group consisting of aspartate, glutamate, serine, threonine and cysteine; (h) a substitution of a lysine residue corresponding to position 198, 199, 205, 208, 209, 211 or 214 of SEQ ID NO: 2 with a residue selected from the group consisting of non-polar amino acids, polar amino acids, and acidic amino acids; (i) a substitution of a polar or non-polar amino acid for a residue corresponding to a position of SEQ ID NO: 2 selected from the group consisting of Phe197, Asn200, Asp204, Glu207, Asp210, Asp212 and Gly213; and (j) a non-conservative substitution of a serine residue corresponding to position 39 of SEQ ID NO: 2.

2. A substantially pure polysaccharide lyase as in claim 1 wherein the substitution comprises a substitution of a cysteine residue corresponding to position 135 of SEQ ID NO: 2 with a residue selected from the group consisting of aspartate, glutamate, serine, threonine, and histidine.

3. A substantially pure polysaccharide lyase as in claim 2 wherein at least a second amino acid residue has been substituted and wherein the second substitution comprises a conservative substitution of a residue of a Cardin-Weintraub-like heparin binding sequence XBBXXXBXB (SEQ ID NO: 3) corresponding to positions 197–205 of SEQ ID NO: 2 wherein the conservative substitution includes the replacement of a basic residue, B, with a basic amino acid or replacement of a non-basic residue, X, with an amino acid which is a conservative substitution.

4. A substantially pure polysaccharide lyase as in claim 2 wherein at least a second amino acid residue has been substituted and wherein the second substitution comprises a conservative substitution of a residue of an EF-hand-like calcium binding sequence of SEQ ID NO:9 corresponding to positions 206–220 of SEQ ID NO:2.

5. A substantially pure polysaccharide lyase as in claim 2 wherein at least a second amino acid residue has been substituted and wherein the second substitution comprises a conservative substitution of a residue of a turn of a PB1, PB2 or PB3 β-sheet domain of SEQ ID NO: 2.

6. A substantially pure polysaccharide lyase as in claim 1 wherein the substitution comprises a conservative substitution of a residue of a Cardin-Weintraub-like heparin binding sequence XBBXXXBXB corresponding to positions 197–205 of SEQ ID NO: 2 with a residue which conforms to the heparin binding sequence.

7. A substantially pure polysaccharide lyase as in claim 6 wherein the substitution comprises a substitution of a lysine residue corresponding to position 198, 199 or 205 of SEQ ID NO: 2 with an arginine or histidine.

8. A substantially pure polysaccharide lyase as in claim 6 wherein the substitution comprises a conservative substitution of a histidine residue corresponding to position 203 of SEQ ID NO: 2.

9. A substantially pure polysaccharide lyase as in claim 1 wherein the substitution comprises a conservative substitution of a residue of an EF-hand-like calcium binding sequence of SEQ ID NO:9 corresponding to positions 206–220 of SEQ ID NO: 2.

10. A substantially pure polysaccharide lyase as in claim 9 wherein the substitution comprises a substitution of a lysine residue corresponding to position 208, 209, 211 or 214 of SEQ ID NO: 2 with an arginine or histidine.

11. A substantially pure polysaccharide lyase as in claim 9 wherein the substitution comprises a substitution of an aspartate residue corresponding to positions 210 or 212 of SEQ ID NO: 2 with a glutamate.

12. A substantially pure polysaccharide lyase as in claim 1 wherein the substitution comprises a substitution of a serine residue corresponding to position 39 of SEQ ID NO: 2 with a alanine residue.

13. A pharmaceutical preparation comprising a sterile formulation of the substantially pure polysaccharide lyase of claim 1 and a pharmaceutically acceptable carrier.

14. An isolated nucleic acid comprising
   an isolated nucleic acid encoding the substantially pure polysaccharide lyase of claim 1.

15. A recombinant host cell including an isolated nucleic acid as in claim 14.

16. An expression vector including an isolated nucleic acid as in claim 14.

17. A substantially pure polysaccharide lyase comprising:
   a modified enzymatically active heparinase I having a modified heparinase I $k_{cat}$ value, wherein the modified heparinase I $k_{cat}$ value is less than 75% of a native heparinase I $k_{cat}$ value.

18. A method of removing active heparin from a heparin containing fluid comprising:
   contacting a heparin containing fluid with the substantially pure polysaccharide lyase as in claims 1 or 17.

* * * * *